(12) United States Patent
Ohtsuka

(10) Patent No.: US 8,039,267 B2
(45) Date of Patent: Oct. 18, 2011

(54) DETECTION METHOD, DETECTION APPARATUS, AND SAMPLE CELL AND KIT FOR DETECTION

(75) Inventor: Hisashi Ohtsuka, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/501,923

(22) Filed: Jul. 13, 2009

(65) Prior Publication Data

US 2010/0009458 A1   Jan. 14, 2010

(30) Foreign Application Priority Data

Jul. 14, 2008 (JP) .................. 2008-182227

(51) Int. Cl.
*G01N 21/75* (2006.01)

(52) U.S. Cl. ......... 436/166; 436/63; 436/164; 436/172; 436/518; 436/527; 436/805; 422/82.08; 435/287.1

(58) Field of Classification Search ........................ None
See application file for complete search history.

(56) References Cited

U.S. PATENT DOCUMENTS

| 6,194,223 | B1 | 2/2001 | Herrmann et al. | |
|---|---|---|---|---|
| 7,022,515 | B2 * | 4/2006 | Herron et al. | 435/287.1 |
| 2005/0053974 | A1 | 3/2005 | Lakowicz et al. | |
| 2006/0181701 | A1 | 8/2006 | Tomaru | |
| 2006/0234396 | A1 | 10/2006 | Tomita et al. | |
| 2007/0118936 | A1 | 5/2007 | Matsunami | |
| 2007/0158549 | A1 | 7/2007 | Naya et al. | |
| 2009/0142847 | A1 * | 6/2009 | Geddes et al. | 436/63 |

FOREIGN PATENT DOCUMENTS

| JP | 09-257702 | 10/1997 |
|---|---|---|
| JP | 2005-077338 A | 3/2005 |
| JP | 2007-085770 A | 4/2007 |

OTHER PUBLICATIONS

Bagwe, Rahul P., et al. Surface modification of silica nanoparticles to reduce aggregation and nonspecific binding, 2006, Langmuir, 22, pp. 4357-4362.*

(Continued)

*Primary Examiner* — Yelena G Gakh
*Assistant Examiner* — Robert Xu
(74) *Attorney, Agent, or Firm* — Sughrue Mion, PLLC

(57) ABSTRACT

A sensor-chip includes a sensor-portion having at least a metal-layer deposited on a surface of a dielectric-plate. A fluorescent-label binding-substance in an amount corresponding to the amount of a detection-target-substance in a liquid-sample binds onto the sensor-portion. The amount of the detection-target-substance is detected based on the amount of light generated by excitation of a fluorescent-label in the fluorescent-label binding-substance. A fluorescent-substance the charge state of which changes in the liquid-sample according to the pH of the liquid-sample, and which contains a plurality of fluorescent-dye-molecules enclosed by a material that transmits fluorescence output from the fluorescent-dye-molecules, is used as the fluorescent-label. With the fluorescent-label binding-substance bound to the sensor-portion, the fluorescent-label is attracted to the sensor-portion by adjusting the pH of the sample-liquid to neutralize the charge state of the fluorescent-substance, thereby attracting the fluorescent-label onto the sensor-portion. In this state, the amount of the detection-target-substance is detected.

6 Claims, 15 Drawing Sheets

OTHER PUBLICATIONS

Liebermann et al., "Surface-plasmon field-enhanced fluorescence spectroscopy," Colloids and Surfaces A, Physiochemical Engineering Aspects, 2000, vol. 171, pp. 115-130.

Tsuboi et al., "High-sensitivity sensing of catechol amines using by optical waveguide mode enhanced fluorescence spectroscopy," 54th Meeting of the Japan Society of Applied Physics and Related Societies, Collection of Abstracts of Lectures, No. 3, p. 1378, 28p-SA-4, Spring 2007, 4 pages including translation.

Vareiro et al., "Surface Plasmon Fluorescence Measurements of Human Chorionic Gonadotrophin: Role of Antibody Orientation in Obtaining Enhanced Sensitivity and Limit of Detection," Analytical Chemistry, Apr. 15, 2005, vol. 77, 2426-2431.

* cited by examiner

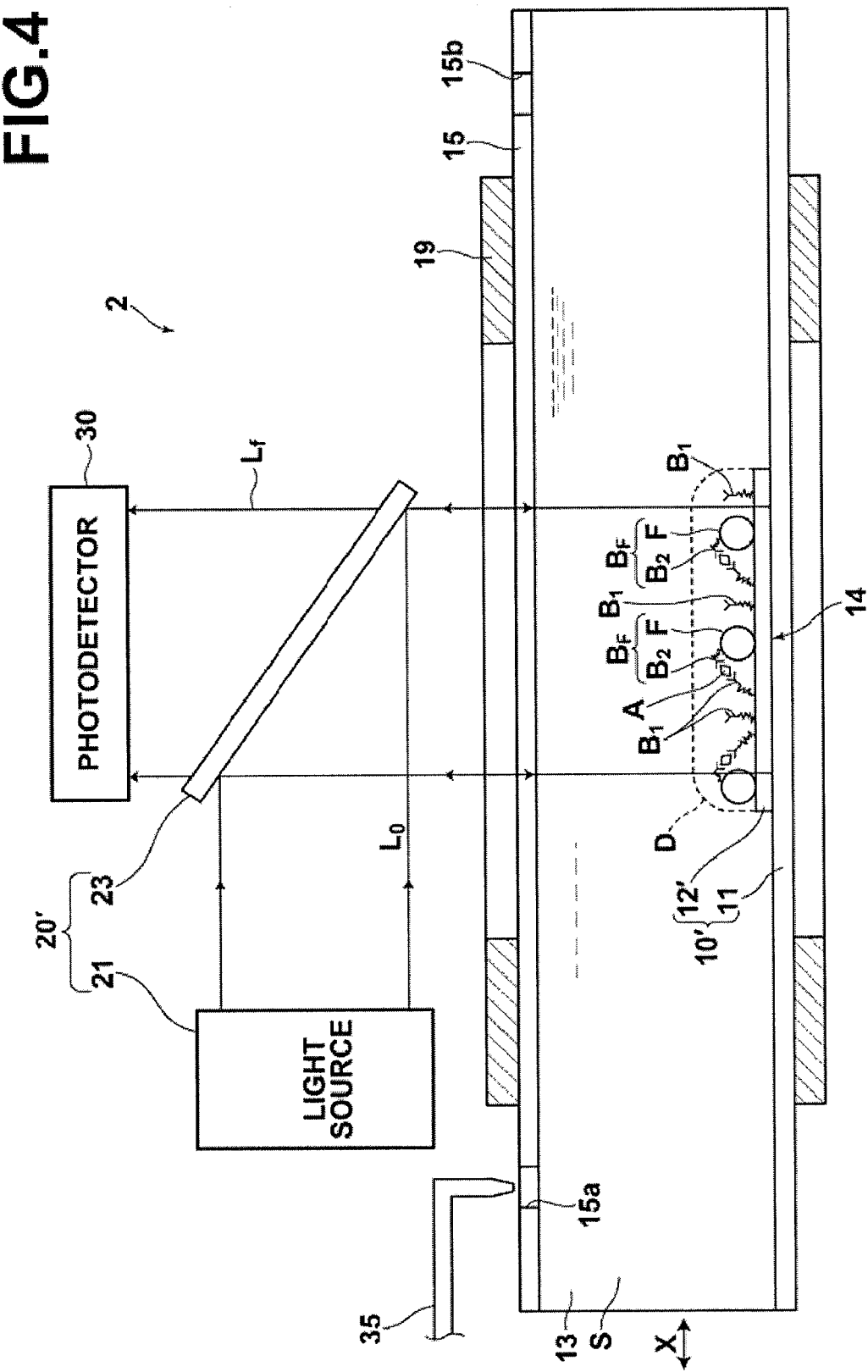

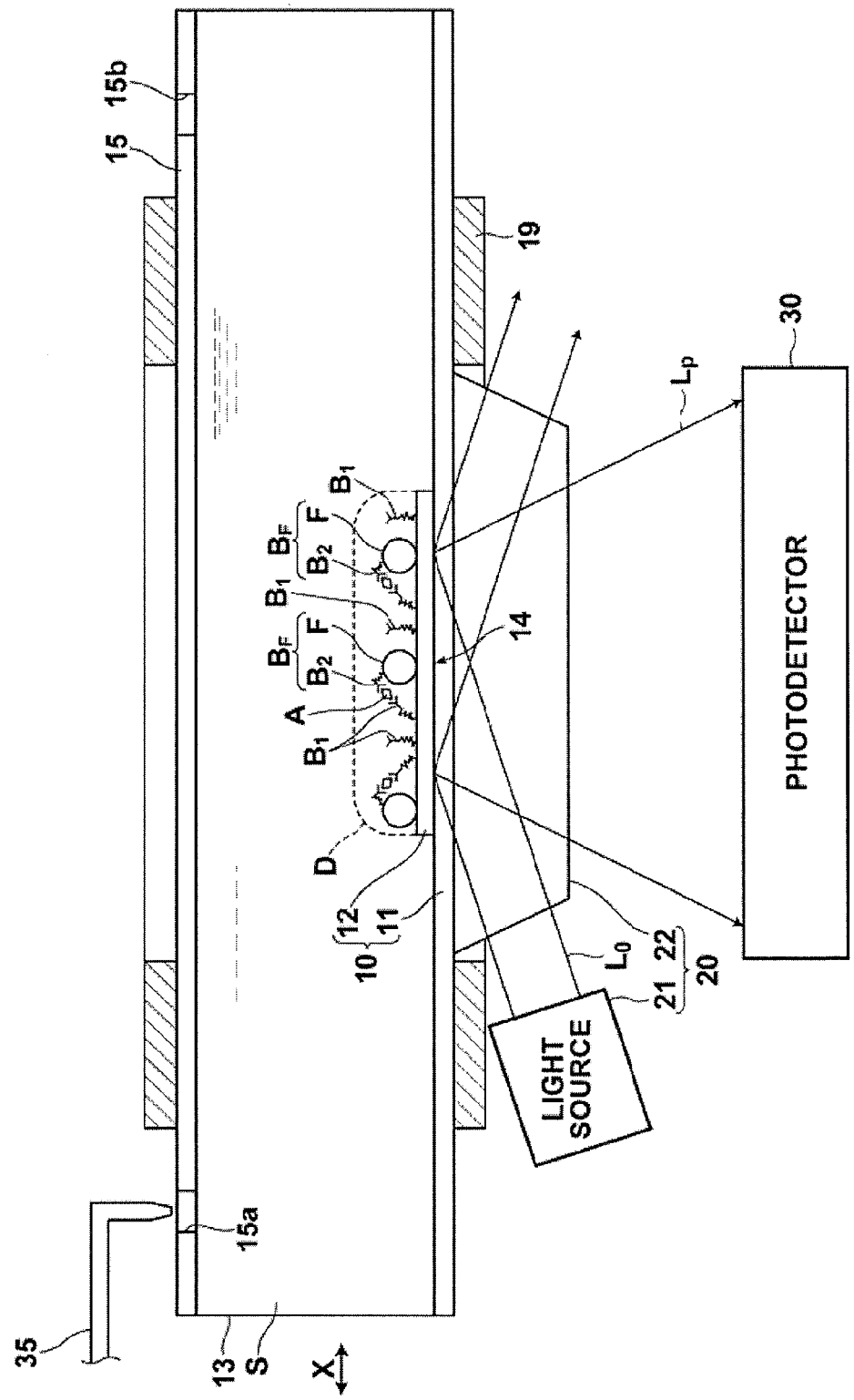

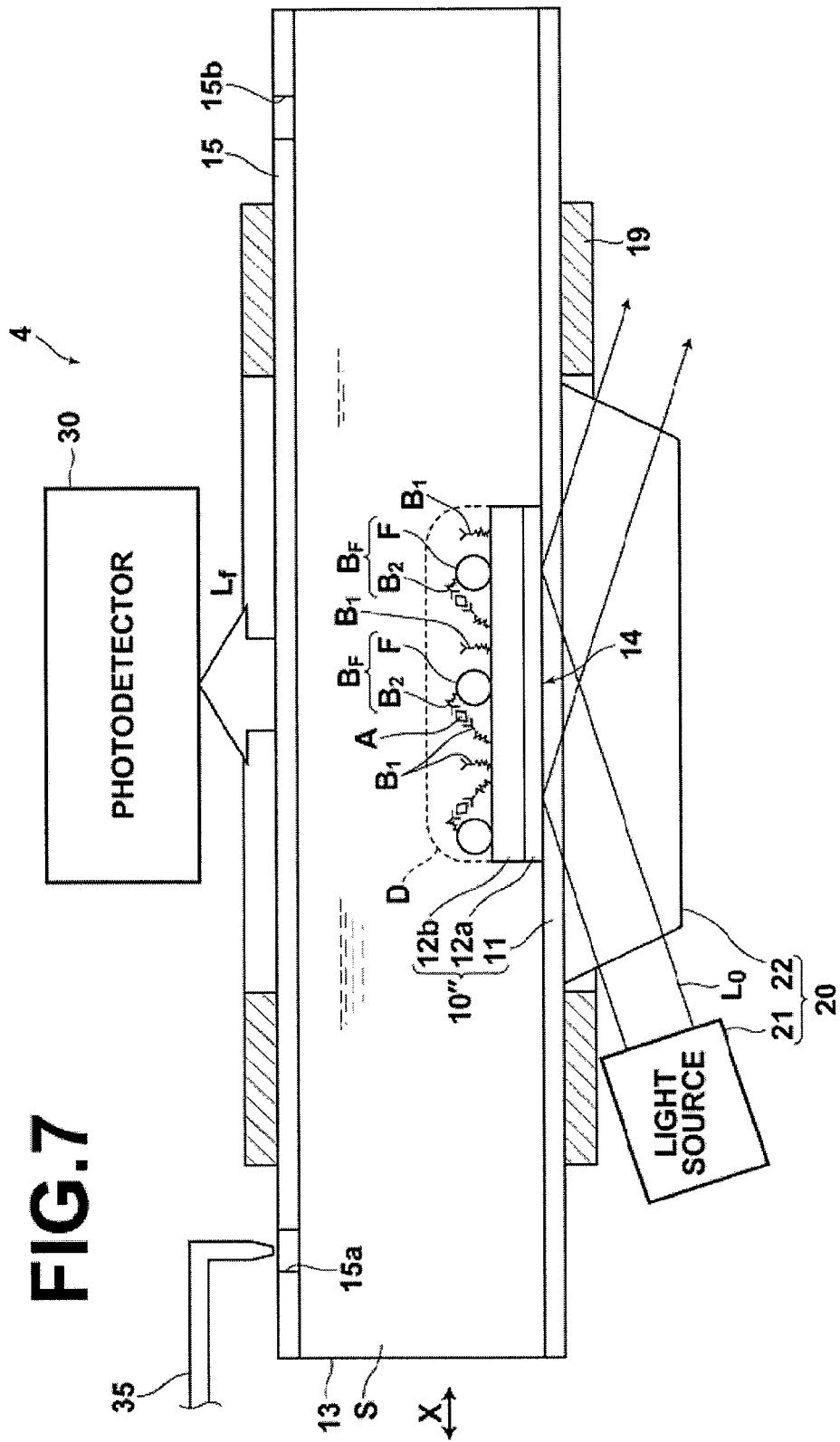

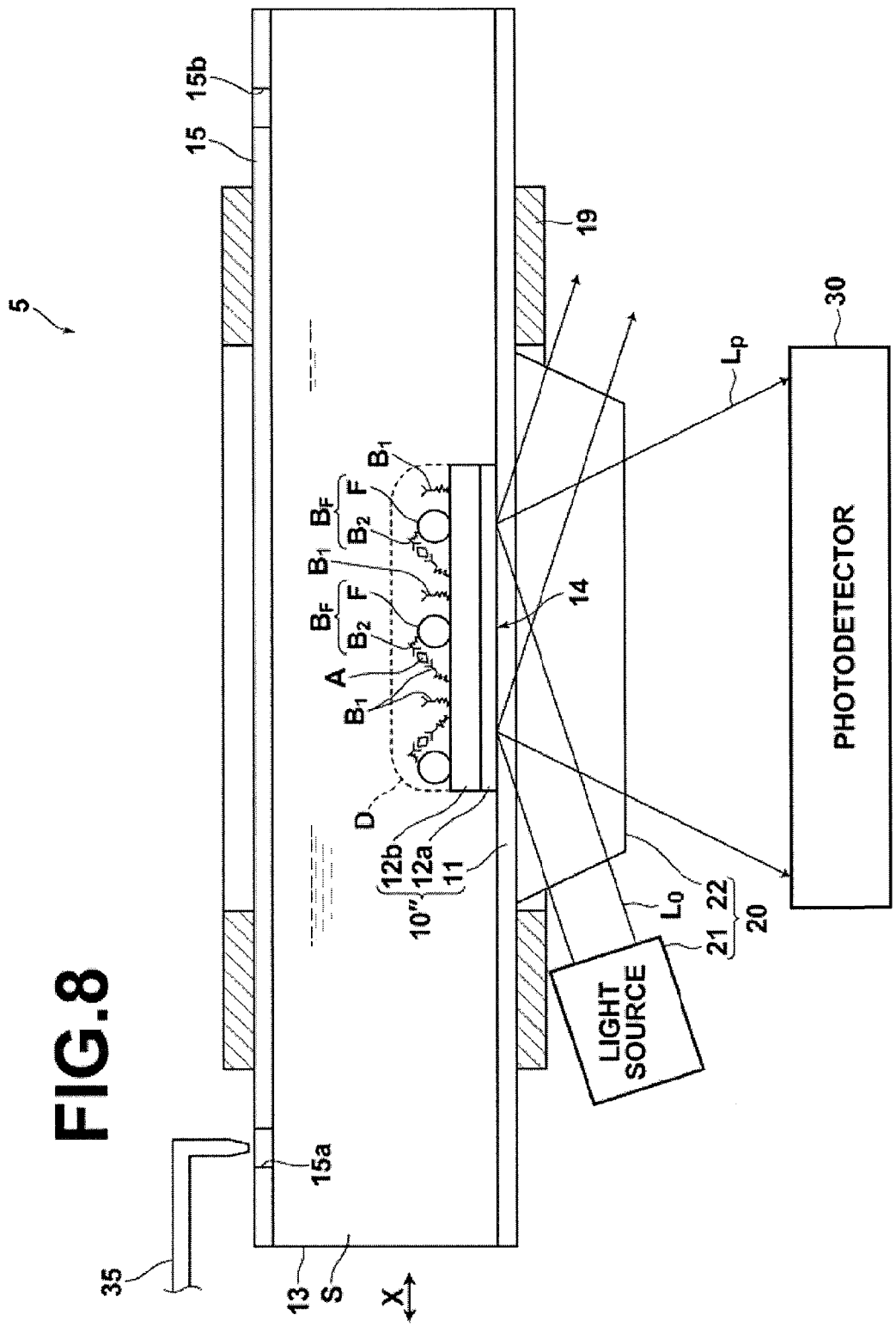

pH DEPENDENCE OF SIGNAL INTENSITY
(MICROPARTICLE SURFACE –COOH, CONTAINING NaCl of 150 mM)

DETECTION METHOD, DETECTION APPARATUS, AND SAMPLE CELL AND KIT FOR DETECTION

BACKGROUND OF THE INVENTION

1. Field of the Invention

The present invention relates to a detection method, a detection apparatus, a sample cell for detection and a kit for detection to detect a substance to be detected (a detection target substance) in a sample.

2. Description of the Related Art

Conventionally, in the field of bio-measurement and the like, a fluorescence detection method is widely used as a highly accurate and easy measurement method. In the fluorescence detection method, a sample that is presumed to contain a detection target substance that outputs fluorescence by being excited by irradiation with light having a specific wavelength is irradiated with excitation light having the specific wavelength. At this time, fluorescence is detected to confirm the presence of the detection target substance. Further, when the detection target substance is not a phosphor (fluorescent substance), a substance that has been labeled with a fluorescent dye and that specifically binds to the detection target substance is placed in contact with the sample. Then, fluorescence from the fluorescent dye is detected in a manner similar to the aforementioned method, thereby confirming the presence of the bond between the detection target substance and the substance that specifically binds to the detection target substance. In other words, presence of the detection target substance is confirmed, and this method is widely used.

In bio-measurement, an assay is performed, for example, by using a sandwich method, a competition method or the like. In the sandwich method, when an antigen, as a detection target substance, contained in a sample needs to be detected, a primary antibody that specifically binds to the detection target substance is immobilized on a substrate (base), and a sample is supplied onto the substrate to make the detection target substance specifically bind to the primary antibody. Further, a secondary antibody to which a fluorescent label has been attached, and that specifically binds to the detection target substance, is added to make the secondary antibody bind to the detection target substance. Accordingly, a so-called sandwich structure of (primary antibody)-(detection target substance)-(secondary antibody) is formed, and fluorescence from the fluorescent label attached to the secondary antibody is detected. In the competition method, a competitive secondary antibody that competes with the detection target substance, and that specifically binds to a primary antibody, and to which a fluorescent label has been attached, binds to the primary antibody in such a manner to compete with the detection target substance. Further, fluorescence from the competitive secondary antibody that has bound to the primary antibody is detected.

When the assay is performed as described above, an evanescent fluorescence method has been proposed. In the evanescent fluorescence method, fluorescence is excited by evanescent light to detect fluorescence only from the secondary antibody that has bound, through the detection target substance, to the primary antibody immobilized on the substrate, or fluorescence only from the competitive secondary antibody that has directly bound to the primary antibody. In the evanescent fluorescence method, fluorescence excited by evanescent waves that extend from the surface of the substrate is detected. The evanescent waves are generated by making excitation light that totally reflects on the surface of the substrate enter the substrate from the back side of the substrate.

Japanese Unexamined Patent Publication No. 2005-077338 (Patent Literature 1) proposes an evanescent fluorescence method. In the evanescent fluorescence method disclosed in Patent Literature 1, instead of immobilizing the primary antibody on the substrate, a bound product (bound substance) of (primary reaction body)-(detection target substance)-(secondary reaction body) is formed in liquid phase. Further, the bound product is localized in an area to which the evanescent waves extend, and fluorescence from the bound product is detected. Specifically, the primary reaction body that includes a primary antibody and a magnetic material and the secondary reaction body that includes a fluorescent substance and the secondary antibody are bound to the detection target substance to obtain the bound product. The magnetic material contained in the primary reaction body is attracted by a magnet, and the bound product is localized.

Meanwhile, in the evanescent fluorescent method, methods using electric-field enhancement effects by plasmon resonance are proposed to improve the sensitivity of detection in U.S. Pat. No. 6,194,223 (Patent Literature 2), M. M. L. M Vareiro et al., "Surface Plasmon Fluorescence Measurements of Human Chorionic Gonadotrophin: Role of Antibody Orientation in Obtaining Enhanced Sensitivity and Limit of Detection", Analytical Chemistry, Vol. 77, pp. 2426-2431, 2005 (Non-Patent Literature 1), and the like. In a surface plasmon enhancement fluorescence method, a metal layer is provided on the substrate, and excitation light is caused to enter the interface between the substrate and the metal layer from the back side of the substrate at an angle greater than or equal to a total reflection angle to generate surface plasmon resonance in the metal layer. Further, fluorescent signals are enhanced by the electric field enhancement action of the surface plasmons to improve the S/N (signal to noise) ratio.

Similarly, in the evanescent fluorescence method, a method using electric field enhancement effects by a waveguide mode is proposed in Spring 2007, the Japan Society of Applied Physics, Collection of Presentation Abstracts, No. 3, p. 1378 (Non-Patent Literature 2). In this optical waveguide mode enhanced fluorescence spectroscopy (OWF), a metal layer and an optical waveguide layer including a dielectric and the like are sequentially formed on the substrate. Further, excitation light is caused to enter the substrate from the back side of the substrate at an angle that is greater than or equal to the total reflection angle to induce an optical waveguide mode in the optical waveguide layer by irradiation with the excitation light. Further, fluorescent signals are enhanced by the electric field enhancement effect by the optical waveguide mode.

Further, Specification of U.S. Patent Application Publication No. 20050053974 (Patent Literature 3) and T. Liebermann and W. Knoll, "Surface-plasmon field-enhanced fluorescence spectroscopy", Colloids and Surfaces A, Vol. 171, pp. 115-130, 2000 (Non-Patent Literature 3) propose a method for extracting radiation light (SPCE: Surface Plasmon-Coupled Emission) from the prism side. In the method, instead of detecting fluorescence output from a fluorescent label excited in the electric field enhanced by surface plasmons, the fluorescence newly induces surface plasmons in the metal layer, and radiation light by the newly induced plasmons is extracted from the prism side.

As described above, in bio-measurement or the like, various kinds of methods have been proposed as a method for detecting the detection target substance. In the methods, plasmon resonance or an optical waveguide mode is induced by irradiation with excitation light, and a fluorescent label is excited in an electric field enhanced by the plasmon resonance or the optical waveguide mode, and the fluorescence is directly or indirectly detected.

Further, in surface plasmon resonance measurement apparatuses, methods for increasing the concentration of detection target substance in a region on the sensor portion, the region to which evanescent waves extend from the sensor portion, are proposed in Japanese Unexamined Patent Publication No. 9(1997)-257702 (Patent Literature 4), Japanese Unexamined Patent Publication No. 2007-085770 (Patent Literature 5), and the like. In Patent Literature 4, Patent Literature 5 and the like, voltage is applied to a sample to attract the detection target substance to the sensor portion, and measurement is performed. In these methods, the pH (potential of hydrogen) of a buffer solution is adjusted to adjust the charge state of a detection target substance, such as protein and nucleic acid. Further, voltage is applied in a state in which the detection target substance is positively or negatively electrified, thereby attracting the detection target substance to the sensor portion.

The method for localizing the detection target substance by application of voltage can achieve a certain effect. Further, Patent Literature 4 describes that in surface plasmon resonance measurement apparatuses, when the detection target substance is attracted to a region within approximately 100 nm from the sensor portion, which the evanescent waves reach, it is possible to reduce the variation in signals.

However, since both of the size and the charge of the detection target substance are small, the attraction effect by application of voltage is weaker than Brown motion of the detection target substance. Therefore, it is difficult to efficiently attract the detection target substance to the surface of the sensor portion. Further, it is necessary to provide a means for applying voltage to the liquid sample. Therefore, there is a problem that the structure of the apparatus becomes complicated.

Further, the electric field enhancement effects by surface plasmon resonance and optical guide mode sharply attenuate as a distance from the surface of the metal layer or the optical waveguide layer increases. Therefore, there is a problem that when the distances from the surface to the fluorescent labels even slightly change, signals from the fluorescent labels become different from each other, and varied. Hence, it is necessary to attract the fluorescent labels within a range of approximately 50 nm from the surface.

For example, FIG. 20 is a schematic diagram illustrating an apparatus for detecting fluorescence by an electric field enhancement effect by surface plasmon resonance. In FIG. 20, the vicinity of a sensor portion of the apparatus is illustrated. A gold film (thin-film, coating or layer) 102 is deposited on a surface of a prism (substrate) 101. Further, primary antibody $B_1$ is immobilized on the gold film 102. When a sandwich assay is performed, fluorescence from a fluorescent label (fluorescent dye molecule f in this case) attached to labeling secondary antibody $B_2$ is detected. The labeling secondary antibody $B_2$ binds to the primary antibody $B_1$ through antigen A. Excitation light is caused to enter the interface between the prism 101 and the gold film 102 at an angle greater than or equal to the total reflection angle to excite surface plasmons on the surface of the gold film 102. Accordingly, the electric field on the surface of the gold film 102 is enhanced. The fluorescent label (fluorescent dye molecule) f is excited in the enhanced electric field, and fluorescence is output. In FIG. 20, the graph shows distance-dependent characteristic of the strength (magnitude) of the electric field, the distance being measured from the surface of the sensor portion (surface of the gold film). As the graph shows, the strength of the electric field sharply decreases as the distance from the surface increases.

At this time, the maximum distance from the surface of the sensor portion to the fluorescent label f of the labeling secondary antibody is approximately 50 nm. When the distance from the surface of the sensor portion is approximately 50 nm, the intensity of fluorescence attenuates by 30% or more. Further, the primary antibody $B_1$ is not always immobilized upright on the surface of the sensor portion, and the primary antibody $B_1$ may fall along the surface by the flow of liquid, a three-dimensional obstacle or the like, and be immobilized in a lying or inclined state. Consequently, the distance from the surface of the fluorescent label f to the surface of the sensor portion is varied, and the intensity of the signal is varied.

SUMMARY OF THE INVENTION

In view of the foregoing circumstances, it is an object of the present invention to provide a detection method and apparatus that can prevent variation (unevenness) in the intensities of signals, and that can efficiently utilize enhanced electric fields, and that can directly or indirectly detect fluorescence, without complicating the structure of the apparatus.

Further, it is another object of the present invention to provide a sample cell and a kit for detection that are used in the detection method of the present invention.

A detection method of the present invention is a detection method comprising the steps of:

preparing a sensor chip including a dielectric plate and a sensor portion that has at least a metal layer deposited on a surface of the dielectric plate;

binding a fluorescent-label binding substance in an amount corresponding to the amount of a detection target substance contained in a liquid sample to the sensor portion by contacting the liquid sample with the sensor portion;

irradiating the sensor portion with excitation light to generate an enhanced optical field on the sensor portion; and detecting the amount of the detection target substance based on the amount of light generated by excitation of a fluorescent label contained in the fluorescent-label binding substance, the fluorescent label being excited in the enhanced optical field, wherein a fluorescent substance the charge state of which changes in the liquid sample according to the pH of the liquid sample is used as the fluorescent substance of the fluorescent label, the fluorescent substance containing a plurality of fluorescent dye molecules enclosed by a material that transmits fluorescence output from the plurality of fluorescent dye molecules, and wherein in the state in which the fluorescent-label binding substance has bound to the sensor portion, the fluorescent substance is attracted to a surface of the sensor portion by adjusting the pH of the liquid sample in such a manner to neutralize the charge state of the fluorescent substance, and wherein the amount of the detection target substance is detected in the state in which the fluorescent substance is attracted to the surface of the sensor portion.

It is desirable that the particle size of the fluorescent substance is greater than or equal to 30 nm. Further, it is more desirable that the particle size of the fluorescent substance is greater than or equal to 70 nm.

In the specification of the present application, when the particle of the fluorescent substance has substantially spherical form, the size of the particle of the fluorescent substance is the diameter of the particle. When the particle does not have spherical form, an average length of the maximum width and the minimum width of the particle is defined as the size of the particle.

Here, the "fluorescent-label binding substance" is a binding substance to which a fluorescent label has been attached.

The binding substance in an amount corresponding to the amount of the detection target binds to the surface of the sensor portion. For example, when an assay by a sandwich method is performed, the fluorescent-label binding substance contains a fluorescent label and a binding substance that specifically binds to the detection target substance. When an assay by a competition method is performed, the fluorescent-label binding substance contains a fluorescent label and a binding substance that competes with the detection target substance.

Further, the expression "detecting the amount of the detection target substance" means detecting presence of the detection target substance as well as detecting the amount of the detection target substance. Further, the amount of the detection target substance may mean not only the quantitative amount of the detection target substance but the qualitative value of the detection target substance.

In the detection method of the present invention, it is desirable that a fluorescent substance the surface of which is modified with a functional group, the charge state of the functional group changing according to the pH of the liquid sample, is used as the fluorescent substance of the fluorescent label, and that when the fluorescent-label binding substance binds to the sensor portion, the pH of the liquid sample is adjusted so as to ionize the functional group, and that after the fluorescent-label binding substance has bound to the sensor portion, the pH of the liquid sample is adjusted so as to neutralize (electrically neutralize) the functional group, thereby attracting the fluorescent substance to the surface of the sensor portion.

Here, the term "optical field" refers to an electric field generated by evanescent light excited by irradiation with excitation light or by near field light.

Further, the expression "generate an enhanced optical field" means that an enhanced optical field is formed by enhancing the optical field. The optical field may be enhanced by plasmon resonance or excitation of optical waveguide mode.

Further, in the method for "detecting the amount of the detection target substance based on the amount of light generated by excitation of a fluorescent label contained in the fluorescent-label binding substance", fluorescence from the fluorescent label may be detected directly. Alternatively, the fluorescence may be detected indirectly.

Specifically, the amount of the detection target substance may be detected, for example, in any of the following manners (1) to (4):

(1) Plasmons are excited in a metal layer by irradiation with excitation light, and an enhanced optical field is generated by the plasmons. Further, the amount of the detection target substance is detected by detecting, as light generated by excitation of the fluorescent label, fluorescence output from the fluorescent label by excitation of the fluorescent label;

(2) Plasmons are excited in the metal layer by irradiation with the excitation light, and an enhanced optical field is generated by the plasmons. Further, the amount of the detection target substance is detected by detecting, as light generated by excitation of the fluorescent label, radiation light that radiates from the opposite surface of the dielectric plate. The radiation light radiates by newly inducing plasmons in the metal layer by fluorescence output from the fluorescent label by excitation of the fluorescent label;

(3) The sensor chip includes an optical waveguide layer deposited on the metal layer. An optical waveguide mode is excited in the optical waveguide layer by irradiation with the excitation light, and an enhanced optical field is generated by the optical waveguide mode. Further, the amount of the detection target substance is detected by detecting, as the light generated by excitation of the fluorescent label, fluorescence output from the fluorescent label by excitation of the fluorescent label; and (4) The sensor chip includes an optical waveguide layer deposited on the metal layer. An optical waveguide mode is excited in the optical waveguide layer by irradiation with the excitation light, and an enhanced optical field is generated by the optical waveguide mode. Further, the amount of the detection target substance is detected by detecting, as the light generated by excitation of the fluorescent label, radiation light that radiates from the opposite-surface of the dielectric plate. The radiation light radiates by newly inducing plasmons in the metal layer by fluorescence output from the fluorescent label by excitation of the fluorescent label.

In the methods (1) and (2), the metal layer may be a metal film (coating, thin-film or the like). Further, excitation light may be caused to enter the interface between the metal film and the substrate from the back side of the substrate at an angle greater than or equal to the total reflection angle to excite surface plasmons on the surface of the metal film. Alternatively, the metal layer may be formed by a metal fine structure body having an uneven pattern on the surface thereof, and the uneven pattern may include projections and depressions at cycles smaller than the wavelength of the excitation light. Alternatively, the metal layer may include a plurality of metal nanorods smaller than the wavelength of the excitation light. The metal layer may be formed in such a manner that localized plasmons are excited in the metal fine structure body or the metal nanorods by irradiation with excitation light.

A detection apparatus of the present invention is used in the detection method of the present invention. The detection apparatus of the present invention is a detection apparatus comprising:

a housing unit that houses a sensor chip including a dielectric plate and a sensor portion that has at least a metal layer deposited on a surface of the dielectric plate;

an excitation-light irradiation optical system that irradiates the sensor portion with excitation light;

a light detection means that detects light generated by excitation of the fluorescent label in an enhanced optical field generated on the sensor portion by irradiation with the excitation light; and a pH adjustment means that adjusts the pH of the liquid sample by injecting a pH adjustment liquid to the sensor chip.

A sample cell for detection of the present invention is used in the detection method of the present invention. The sample cell for detection of the present invention is a sample cell comprising:

a base that has a flow path in which a liquid sample flows down;

an injection opening for injecting the liquid sample into the flow path, the injection opening being provided on the upstream side of the flow path;

an air hole for causing the liquid sample that has been injected from the injection opening to flow down toward the downstream side of the flow path, the air hole being provided on the downstream side of the flow path; and a sensor chip portion provided between the injection opening and the air hole in the flow path, wherein the sensor chip portion includes a dielectric plate that is provided at least in a part of the inner wall of the flow path and a sensor portion that has at least a metal layer deposited on a sample-contact surface of the dielectric plate.

In the sample cell for detection, it is desirable that the sensor portion includes an immobilization layer that binds to a fluorescent-label binding substance.

Further, it is desirable that the fluorescent-label binding substance includes, as a fluorescent label, a fluorescent substance the charge state of which changes in the liquid sample according to the pH of the liquid sample, the fluorescent substance containing a plurality of fluorescent dye molecules enclosed by a material that transmits fluorescence output from the plurality of fluorescent dye molecules, and that the fluorescent-label binding substance is immobilized in the flow path on the upstream side of the sensor portion.

In the sample cell of the present invention, when a first binding substance that specifically binds to the detection target substance is immobilized in the immobilization layer, and the fluorescent-label binding substance includes a second binding substance that specifically binds to the detection target substance and binds to the first binding substance through the detection target substance, the sample cell is appropriate to perform an assay by a so-called sandwich method.

In the sample cell of the present invention, when a first binding substance that specifically binds to the detection target substance is immobilized in the immobilization layer, and the fluorescent-label binding substance includes a third binding substance that specifically binds to the first binding substance, competing with the detection target substance, the sample cell is appropriate to perform an assay by a competition method.

Further, an optical waveguide layer may be provided on the metal layer in the sensor portion.

Further, a kit for detection of the present invention is used in the detection method of the present invention. The kit for detection of the present invention is a kit for detection comprising:

a sample cell; and
a solution for labeling,
wherein the sample cell includes:
a base that has a flow path in which a liquid sample flows down;
an injection opening for injecting the liquid sample into the flow path, the injection opening being provided on the upstream side of the flow path;
an air hole for causing the liquid sample that has been injected from the injection opening to flow down toward the downstream side of the flow path, the air hole being provided on the downstream side of the flow path;
a sensor chip portion provided between the injection opening and the air hole in the flow path, the sensor chip including a dielectric plate that is provided at least on a part of the inner wall of the flow path and a sensor portion including at least a metal layer deposited on a sample-contact surface of the dielectric plate; and
an immobilization layer that is immobilized on the sensor portion, and that binds to a fluorescent-label binding substance,
and wherein the solution for labeling contains the fluorescent-label binding substance that includes, as a fluorescent label, a fluorescent substance the charge state of which changes in the liquid sample according to the pH of the liquid sample, the fluorescent substance including a plurality of fluorescent dye molecules enclosed by a material that transmits fluorescence output from the plurality of fluorescent dye molecules, and wherein the solution for labeling is injected into the flow path to flow down in the flow path together with the liquid sample or after the liquid sample has flowed down through the flow path.

In the kit for detection, an optical waveguide layer may be provided on the metal layer in the sensor portion.

In the kit for detection of the present invention, when a first binding substance that specifically binds to the detection target substance is immobilized in the immobilization layer of the sample cell, and the solution for labeling contains the fluorescent-label binding substance that includes a second binding substance that specifically binds to the detection target substance, and which binds to the first binding substance through the detection target substance, the kit for detection of the present invention is appropriate to perform an assay by a sandwich method. Further, when a first binding substance that specifically binds to the detection target substance is immobilized in the immobilization layer of the sample cell, and the solution for labeling contains the fluorescent-label binding substance that includes a third binding substance that specifically binds to the first binding substance, competing with the detection target substance, the kit for detection of the present invention is appropriate to perform an assay by a competition method.

Further, it is desirable that the material of the metal layer contains, as a main component, at least one kind of metal selected from the group consisting of Au, Ag, Cu, Al, Pt, Ni, Ti, and alloys thereof. Here, the term "main component" is defined as a component contained at greater than or equal to 90% by mass.

According to the detection method and apparatus of the present invention, a fluorescent substance the charge state of which changes in the liquid sample according to the pH of the liquid sample, the fluorescent substance including a plurality of fluorescent dye molecules enclosed by a material that transmits fluorescence output from the plurality of fluorescent dye molecules, is used as a fluorescent label of a fluorescent-label binding substance that binds to the sensor portion based on the amount of the detection target substance contained in a sample. Further, in a state in which the fluorescent-label binding substance has bound to the sensor portion, the pH of the liquid sample is adjusted to attract the fluorescent substance to the surface of the sensor portion at which the optical field enhancement effect is high. Further, the fluorescent label contained in the fluorescent-label binding substance is excited, and the amount of light generated by the excitation is detected in the state in which the fluorescent substance is attracted to the surface of the sensor portion. Since the light is detected in such a manner, it is possible to efficiently use the optical field on the surface of the sensor portion at which the degree of enhancement of the optical field is high. Further, since it is possible to make the distances from the surface of the sensor portion to the fluorescent labels uniform (even), variation in the intensity of signals can be prevented. Since the fluorescent substance is attracted to the sensor portion only by adjusting the pH of the liquid sample, it is possible to detect stable signals at an excellent S/N ratio without complicating the structure of the apparatus. Further, it is possible to accurately detect presence and/or the amount of the detection target substance.

When the sample cell for detection of the present invention or the kit for detection of the present invention is used, it is possible to easily carry out the detection method of the present invention. Further, it is possible to effectively use the enhanced optical field, and to prevent variation in the intensity of signals. Further, it is possible to accurately detect presence and/or the amount of the detection target substance.

BRIEF DESCRIPTION OF THE DRAWINGS

FIG. 4 is a schematic diagram illustrating the structure of a fluorescence detection apparatus according to a second embodiment of the present invention;

FIG. 6 is a schematic diagram illustrating the structure of a detection apparatus according to a third embodiment of the present invention;

FIG. 7 is a schematic diagram illustrating the structure of a detection apparatus according to a fourth embodiment of the present invention;

FIG. 8 is a schematic diagram illustrating the structure of a detection apparatus according to a fifth embodiment of the present invention;

DESCRIPTION OF THE PREFERRED EMBODIMENTS

Hereinafter, embodiments of the present invention will be described with reference to the drawings. In each of the diagrams, the size of each unit or element differs from the actual size thereof for the purpose of explanation.

"Detection Method and Apparatus"

Figure 1:
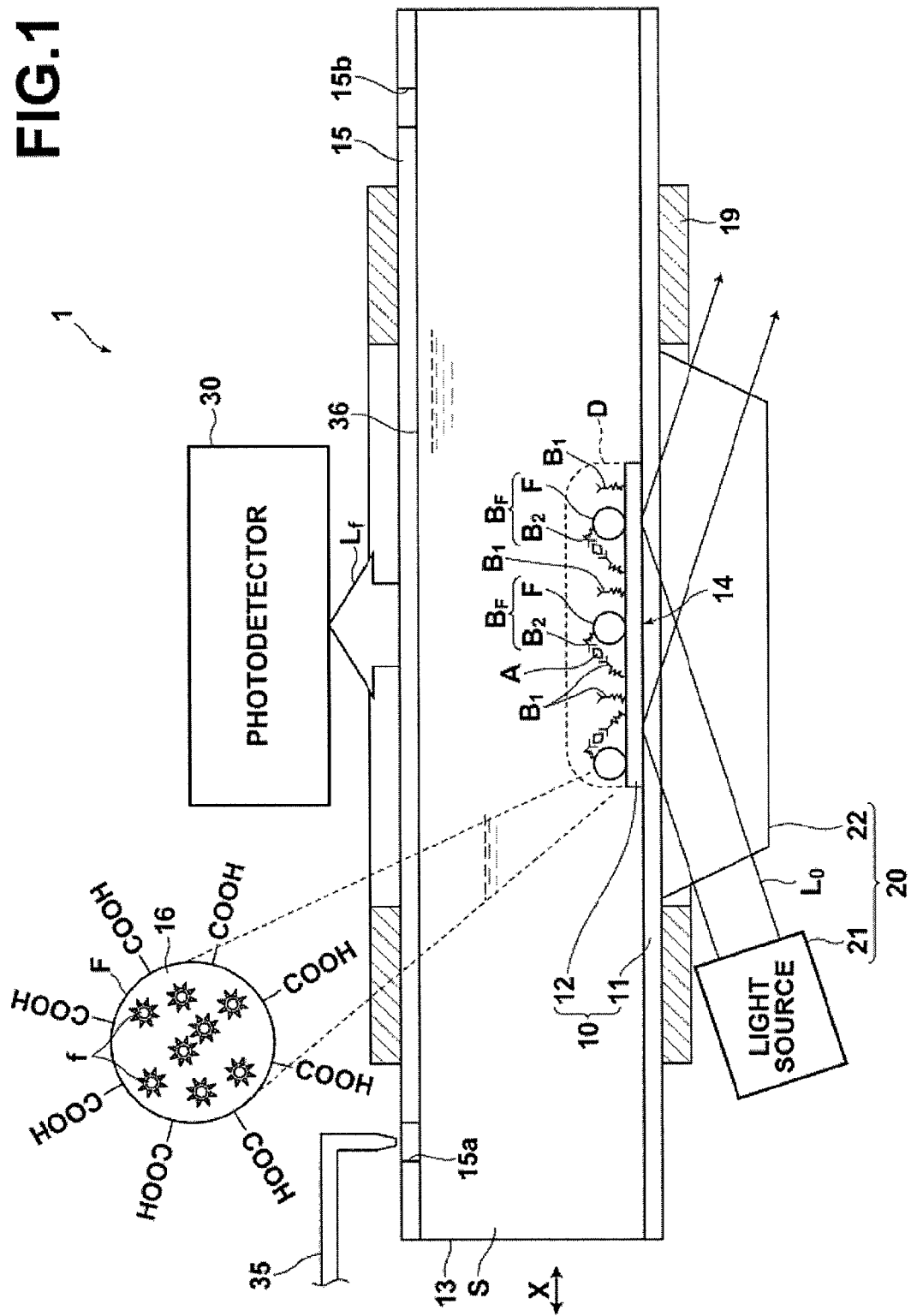
FIG. 1 is a schematic diagram illustrating the structure of a fluorescence detection apparatus according to a first embodiment of the present invention.

In a detection method according to the present invention, for example, a sensor chip 10 including a dielectric plate 11 and a sensor portion 14, as illustrated in FIG. 1, is used. The sensor portion 14 includes at least a metal layer 12 deposited on a surface of the dielectric plate 11. Further, a sample is placed in contact with the sensor portion 14 to make fluorescent-label binding substance $B_F$ in an amount corresponding to the amount of detection target substance A (substance to be detected) contained in the sample bind onto the sensor portion 14. Further, the sensor portion 14 is irradiated with excitation light $L_0$ to generate an enhanced optical field D on the sensor portion 14, and a fluorescent label F in the fluorescent-label binding substance $B_F$ is excited in the enhanced optical field D. Further, the amount of the detection target substance A is detected based on the amount of light generated by excitation of the fluorescent label F. In the detection method of the present invention, a fluorescent substance F the charge state of which changes in the liquid sample according to the pH of the liquid sample, the fluorescent substance including a plurality of fluorescent dye molecules f enclosed by a material that transmits fluorescence output from the plurality of fluorescent dye molecules f, is used as a fluorescent label. Further, in a state in which the fluorescent-label binding substance $B_F$ has bound to the sensor portion 14, the pH of the liquid sample is adjusted so as to neutralize the charge state of the fluorescent substance, thereby attracting the fluorescent substance to the surface of the sensor portion. Further, the amount of detection target substance A is detected in the state in which the fluorescent substance F has been attracted to the sensor portion 14.

As the fluorescent substance the charge state of which changes in the liquid sample according to the pH of the liquid sample, a fluorescent substance the surface of which is modified with a functional group, the charge state of which changes according to the pH of the liquid sample, may be used. At this time, when the fluorescent-label binding substance binds to the sensor portion, the pH of the liquid sample is adjusted to a pH at which the functional group is ionized in the liquid sample. After the fluorescent-label binding substance has bound to the sensor portion, the fluorescent substance can be attracted to the surface of the sensor portion by adjusting the pH of the liquid sample to a pH at which the functional group is neutralized in the liquid sample.

Here, the expression "bind to the sensor portion" means specifically binding to the sensor portion. More specifically, a substance to which the fluorescent-label binding substance specifically binds is provided as the immobilization layer in the sensor portion, and binding to the immobilization layer is an example of biding to the sensor portion.

Further, a detection apparatus of the present invention performs the detection method of the present invention. The detection apparatus includes a housing unit 19 for housing the sensor chip 10, an excitation light irradiation optical system 20, a light detection means 30, and a pH adjustment means 35. The excitation light irradiation optical system 20 irradiates the sensor portion 14 with excitation light $L_0$, and the light detection means 30 detects light in an amount corresponding to detection target substance A, the light being generated by irradiation with the excitation light $L_0$. The pH adjustment means 35 adjusts the pH of the liquid sample by injecting a pH adjustment liquid to the sensor chip. In FIG. 1, only a nozzle portion of the pH adjustment means 35 is illustrated. The nozzle portion is used to inject the pH adjustment liquid.

It is desirable that a fluorescent substance containing a plurality of fluorescent dye molecules f enclosed (included, encapsulated or the like) by a material 16 that transmits fluorescence output from the plurality of fluorescent dye molecules f is used as the fluorescent substance of the fluorescent label. An enlarged view of the plurality of fluorescent dye molecules f enclosed by the material 16 is illustrated in FIG. 1. The fluorescent substance F containing the plurality of fluorescent dye molecules f enclosed by the material 16 is desirable, because it is possible to increase the amount of fluorescence. Further, since the fluorescent dye molecules f are enclosed by the material 16 that transmits fluorescence $L_f$, it is possible to maintain a distance that is longer than or equal to a predetermined distance from the metal layer. Hence, it is possible to prevent metal quenching that occurs when the fluorescent dye molecules f are close to the metal layer 12.

When the fluorescent dye molecules are located too close to the metal layer, quenching occurs due to energy transfer to the metal. When the metal is a flat plane having a semi-infinite thickness, the magnitude (degree) of energy transfer is in inverse proportion to the cube of the distance. When the metal is a flat plane having a finitely thin thickness, the magnitude of energy transfer is in inverse proportion to the fourth power of the distance. Further, when the metal is microparticles, the magnitude of energy transfer is in inverse proportion to the sixth power of the distance. Therefore, it is desirable that the distance between the metal layer 12 and the fluorescent dye molecules f is at least a few nm, and it is more desirable that the distance is greater than or equal to 10 nm.

Conventionally, a method for preventing metal quenching is well known. In the method, a self-assembled monolayer (SAM) is formed on the metal layer 12, and further carboxymethyl dextran (CMD) coating is applied to the SAM to make the metal layer and the fluorescent dye molecule apart from each other. However, formation of such layers or coatings on the metal layer to prevent metal quenching complicates the process of producing the sensor chip, and greatly increases the operation process. In contrast, when the fluorescent substance F, as described above, is used, it is possible to effectively prevent metal quenching by using an extremely simple method without providing the layer or coating for preventing metal quenching.

As the material 16, polystyrene, $SiO_2$, or the like may be used for example. However, the material is not limited to these materials as long as the material can enclose the fluorescent dye molecules f, and transmit fluorescence from the fluorescent dye molecules f to output the fluorescence to the outside of the fluorescent substance.

Further, it is desirable that the size of the fluorescent substance is sufficiently large so that the effect of cohesion of the fluorescent substance to a wall by a drop in the hydrophilicity of the fluorescent substance exceeds the Brown motion of the fluorescent-label binding substance in the liquid sample when the charge (electric charge) of the fluorescent substance is neutralized and the hydrophilicity of the fluorescent substance drops. Examples of protein and biomolecules that may be detected, as the detection target substance, and that have large sizes are antibodies (15 nm or less), albumin (20 nm or less), and the like. However, even if such detection target substances are electrified, the attraction effect is not sufficient. Therefore, it is desirable that the size (diameter) of a particle of the fluorescent substance is approximately 30 nm or more. If the size of the particle is less than 30 nm, there is a risk that a sufficient attraction effect is not achieved because of the Brown action of the substance. Further, when the size of the particle of the fluorescent substance is 70 nm or more, a more effective attraction effect is expected. Further, when the size of the particle of the fluorescent substance is 100 nm or more, an even more effective attraction effect can be expected.

Further, it is desirable that the size of the particle is less than or equal to 5300 nm for diffusion time. Further, when a fluorescence amount, highest-density loading of the substance onto the sensor portion, and surface plasmon disturbance are considered, it is more desirable that the size of the particle is in the range of 70 nm to 900 nm. Further, it is even more desirable that the size of the particle is in the range of 130 nm to 500 nm.

The fluorescent substance F may be produced, for example, as follows:

First, polystyrene particles (Estapor, $\phi$500 nm, 10% solid, carboxyl group, product No. K1-050) are prepared to obtain 0.1% solid in phosphate (polystyrene solution: pH 7.0).

Next, an acetic acid ethyl solution (1 mL) containing 0.3 mg of fluorescent dye molecules (Hayashibara Biochemical Labs., Inc., NK-2014 (excitation ~780 nm)) is produced.

Further, the polystyrene solution and the fluorescent dye solution are mixed together, and impregnated while the mixture evaporates. After then, centrifugation (15000 rpm, 4° C., 20 minutes, twice) is performed, and the supernatant is removed. Accordingly, fluorescent substance F, in which fluorescent dye is enclosed by polystyrene, is obtained. When the fluorescent substance F is produced by impregnating the fluorescent dye into the polystyrene particle through the aforementioned processes, the size or diameter of the particle of the fluorescent substance F is the same as that of polystyrene particle ($\phi$500 nm in the above example). Further, since the surface of the polystyrene particle that is used in the above process is modified with a carboxyl group, the surface of the fluorescent substance F is also modified with the carboxyl group. The carboxyl group is a functional group the charge state of which changes according to pH. The charge state of the fluorescent substance changes according to the pH.

The fluorescent-label binding substance $B_F$ is a binding substance to which a fluorescent label has been attached, and the fluorescent-label binding substance $B_F$ in an amount corresponding to the amount of the detection target substance A binds onto the sensor portion 14. As illustrated in FIG. 1, when an assay is performed by a sandwich method, the fluorescent-label binding substance $B_F$ includes a binding substance that specifically binds to the detection target substance and the aforementioned fluorescent substance F. When an assay is performed by using a competition method, which will be described later, the fluorescent-label binding substance $B_F$ includes a binding substance that competes with the detection target substance and the fluorescent substance F. Specifically, when the sensor chip 10 in which first binding substance $B_1$ that specifically binds to the detection target substance A is immobilized, as an immobilization layer, in the sensor portion 14 is used, the fluorescent-label binding substance $B_F$ including second binding substance $B_2$ that specifically binds to the detection target substance A and fluorescent substance F that is modified with the binding substance $B_2$ is used in the sandwich method. In the competition method, the fluorescent-label binding substance $B_F$ including a third binding substance that competes with the detection target substance A and that specifically binds to the first binding substance $B_1$ and fluorescent substance F that is modified with the third binding substance is used. When the detection target substance A is an antigen, a so-called primary antibody should be used as the first binding substance $B_1$, and a so-called labeling secondary antibody should be used as the fluorescent-label binding substance.

As the functional group that modifies the surface of the fluorescent substance, and the charge state of which changes in the liquid sample according to the pH of the liquid sample, carboxyl group, sulfonic acid group, phosphoric acid group, amino group, quaternary ammonium group, imidazole group, guanidinium group, and the like may be used. For example, the carboxyl group (—COOH) is ionized (COO⁻) at the vicinity of pH 7.4 in a liquid sample, such as a blood serum or blood plasma, or in phosphoric-acid buffer physiologic saline (Phosphate buffered saline, PBS) or the like. When the pH is lowered to approximately pH 5 (specifically, an acetic acid solution is used), COO⁻ protonates, and changes to COOH. Consequently, COO⁻ is electrically neutralized. Further, the amino group (—NH$_2$) is ionized (NH$_3^+$) at the vicinity of approximately pH 7.4 in a liquid sample, such as a blood serum or blood plasma, or in PBS or the like. When the pH is increased to approximately 9 (specifically, a borate buffer solution is used), NH$_3^+$ deprotonates and changes to NH$_2$. Consequently, NH$_3^+$ is electrically neutralized.

Figure 2:
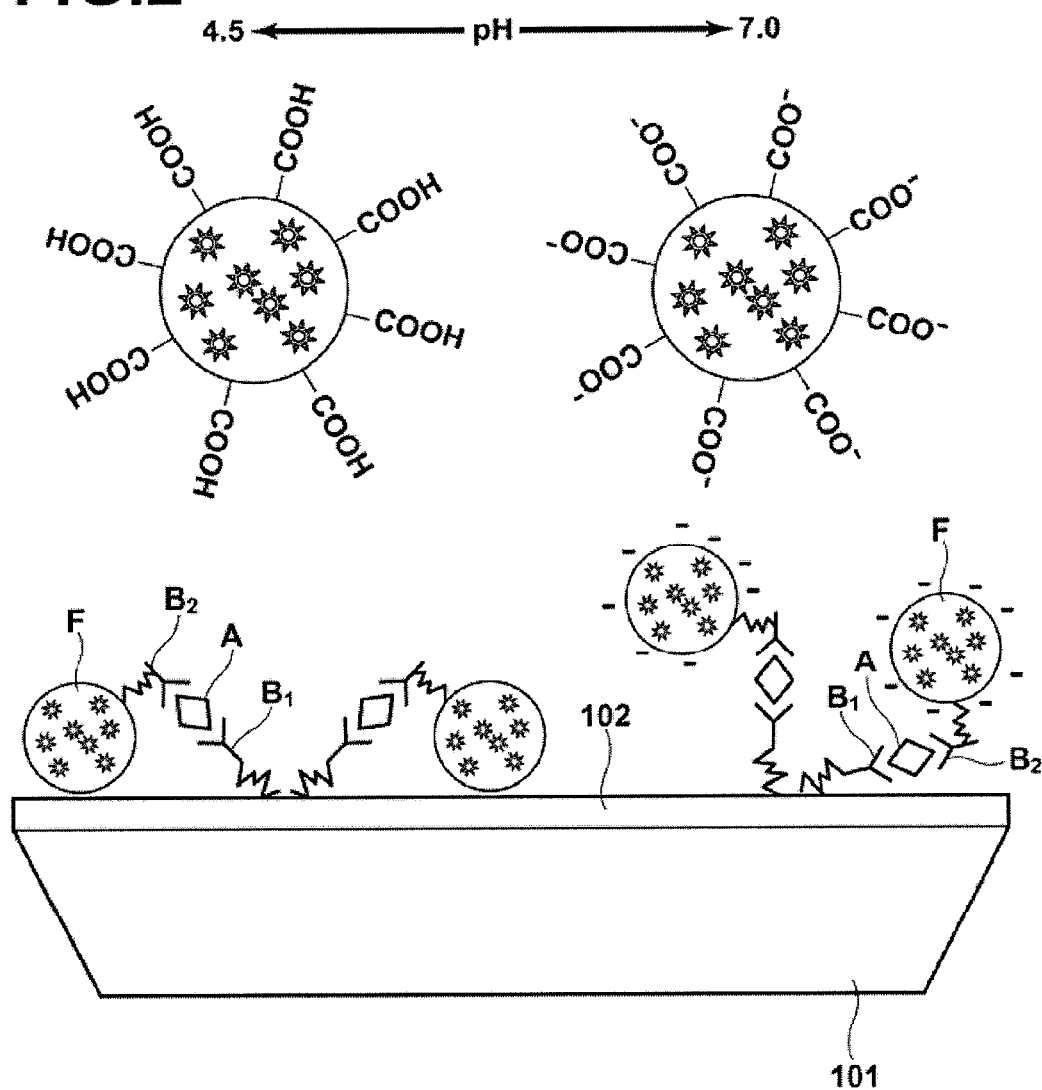
FIG. 2 is a schematic diagram for explaining the pH of liquid sample, charges on the surface of a fluorescent substance, and the dispersion characteristic of the fluorescent substance in the liquid sample.

FIG. 2 is a schematic diagram illustrating the charges on the surface of the fluorescent substance when the pH of the liquid sample is adjusted and the dispersion characteristic of the fluorescent substance in the liquid sampled. Here, a case in which the surface of the fluorescent substance is modified with the functional group of COOH will be described. The functional group is ionized (COO⁻) at the vicinity of pH 7, and particles of the fluorescent substance repel each other because they are charged in the same polarity. Further, since the functional group is ionized, the hydrophilicity is high, and the dispersion characteristic of the fluorescent substance in the liquid sample is high. In contrast, when the functional group is neutralized by lowering the pH of the liquid sampled to 4.5, the hydrophilicity of the fluorescent substance becomes lower, and the fluorescent substance becomes hydrophobic. Therefore, the dispersion characteristic of the fluorescent substance in the liquid sample becomes lower, and the fluorescent substance gathers on the wall side. In other words, when the functional group is neutralized in the state in which the fluorescent-label binding substance has bound to the sensor potion, the fluorescent substance is attracted to the surface of the sensor portion on the closest wall side.

Figure 20:
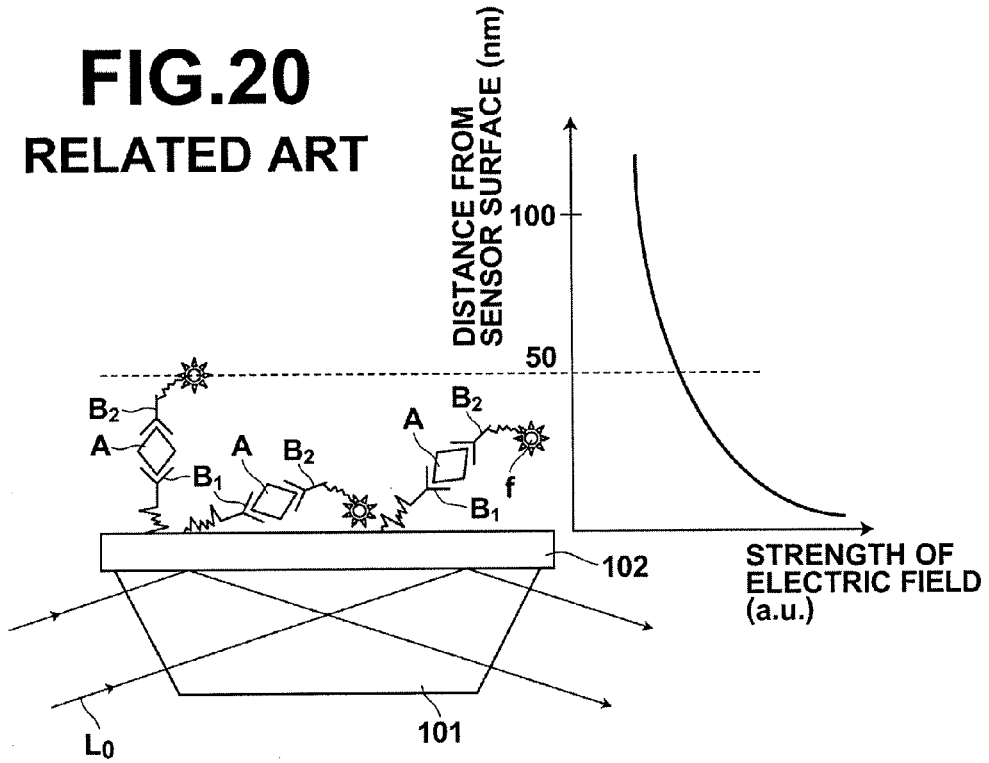
FIG. 20 is a diagram illustrating a conventional example.

In the example illustrated in FIG. 20, which has been described already, the fluorescent label is not sufficiently attracted to the metal layer. Further, the distance from the sensor surface to the fluorescent label is varied because the bond products are upright, lying or the like. However, if the fluorescent substance the charge state of which changes according to the pH of the liquid sample is used, it is possible to efficiently and evenly (uniformly) attract the fluorescent substance to the surface of the sensor merely by controlling the pH of the liquid sample. Hence, it is possible to detect stable signals at an excellent S/N ratio.

In the present invention, the enhanced optical field is generated on the sensor portion by irradiation with excitation light, and light output by excitation of the fluorescent label in the enhanced optical field is detected. The optical field may be enhanced by surface plasmon resonance, or by localized plasmon resonance. Alternatively, the optical field may be enhanced by excitation of an optical waveguide mode. Further, fluorescence output from the fluorescent label may be detected either directly or indirectly. Specific examples will be described in each of the following embodiments.

First Embodiment

A detection method and apparatus according to a first embodiment will be described with reference to FIG. 1. FIG. 1 is a schematic diagram illustrating the structure of the whole detection apparatus of the first embodiment. The detection method and apparatus of this embodiment is a fluorescence detection method and apparatus that enhances an optical field by surface plasmon resonance, and detects fluorescence excited in the enhanced optical field.

In the fluorescence detection method of the present embodiment, a sensor chip 10 including a dielectric plate 11 and a sensor portion 14 that has at least a metal coating (metal film or thin-film or the like), as a metal layer 12, deposited in a predetermined area on a surface of the dielectric plate 11 is used. Further, a sample retaining unit 13 for retaining liquid sample S on the sensor chip 10 is provided. The sensor chip 10 and the sample retaining unit 13 constitute a box-form sample cell that can retain the liquid sample.

The metal layer (film) 12 may be formed on a surface of the dielectric plate 11 by forming (placing) a mask that has an opening in the predetermined area, and by depositing metal by using a well-known vapor-deposition method (evaporation method). It is desirable that the thickness of the metal layer 12 is appropriately determined, based on the material of the metal layer 12 and the wavelength of the excitation light, so that surface plasmons are strongly excited. For example, when a laser beam that has a center wavelength of 780 nm is used as the excitation light, and a gold (Au) film is used as the metal layer 12, it is desirable that the thickness of the metal layer is 50 nm±20 nm. Further, it is more desirable that the thickness is 47 nm±10 nm. Further, it is desirable that the metal layer contains, as a main component, at least one kind of metal selected from the group consisting of Au, Ag, Cu, Al, Pt, Ni, Ti, and alloys thereof.

The detection apparatus 1 of the present invention includes a housing unit 19 that houses the sensor chip 10. The detection apparatus 1 also includes an excitation light irradiation optical system 20, a photodetector 30, and a pH adjustment means 35. The excitation light irradiation optical system 20 causes excitation light $L_0$ to enter the interface between the dielectric plate 11 and the metal layer 12 of the sensor chip 10 housed in the housing unit 19 from the opposite surface of the sensor chip 10, the opposite surface being opposite to the metal-layer-formation surface of the sensor chip 10, at an angle greater than or equal to a total reflection angle. The photodetector 30 detects fluorescence $L_f$ output by irradiation with the excitation light $L_0$. When the sensor chip 10 is housed in the housing unit 19, the pH adjustment means 35 injects pH adjustment liquid to the sensor chip to adjust the pH of the liquid sample.

The excitation-light irradiation optical system 20 includes a light source 21, such as a semiconductor laser (LD), which outputs the excitation light $L_0$. Further, the excitation-light irradiation optical system 20 includes a prism 22 arranged in such a manner that a surface of the prism 22 contacts the dielectric plate 11. The prism 22 guides the excitation light $L_0$ into the dielectric plate 11 so that the excitation light $L_0$ totally reflects at the interface between the dielectric plate 11 and the metal layer 12. Further, the prism 22 and the dielectric plate 11 are in contact with each other through refractive-index-matching oil. The light source 21 is arranged in such a manner that the excitation light $L_0$ enters the prism from another surface of the prism 22 and enters a sample-contact-surface 10$a$ of the sensor chip 10 at an angle greater than or equal to a total reflection angle. Further, the light source 21 is arranged in such a manner that the excitation light $L_0$ enters the metal layer at a specific angle that generates surface plasmon resonance. Further, a light guide member may be arranged between the light source 21 and the prism 22, if necessary. Further, the excitation light $L_0$ is caused to enter the interface between the dielectric plate 11 and the metal layer 12 in a p-polarized light state so as to generate surface plasmons.

As the photodetector 30, a CCD, a PD (photodiode), a photomultiplier, c-MOS or the like may appropriately be used.

The housing unit 19 is structured in such a manner that when the sensor chip 10 is housed in the housing unit 19, the sensor portion 14 of the sensor chip 10 is arranged on the prism 22 and fluorescence is detected by the photodetector 30. The cell (sensor chip 10) can be inserted into the housing unit 19 or removed therefrom in the direction of arrow X in FIG. 1.

In FIG. 1, only the nozzle portion of the pH adjustment means 35 is illustrated. The nozzle portion is used to inject the pH adjustment liquid. Further, the pH adjustment means 35 includes a reservoir chamber for retaining the pH adjustment liquid, and the pH adjustment liquid is dropped out from the nozzle when necessary. In the present embodiment, the detection apparatus is structured in such a manner that the pH adjustment means injects the pH adjustment liquid in the state in which the sensor chip is housed in the housing unit 19. However, the pH may be adjusted before the sensor chip is housed in the housing unit 19. Further, the pH adjustment means may be structured in such a manner that the pH is adjusted before housing.

A fluorescence detection method according to the present invention using the fluorescence detection apparatus 1 will be described.

Here, a case in which antigen A contained in sample S is detected as measurement target substance will be described.

As the sensor chip 10, a sensor chip in which a metal film (metal layer) 12 of the sensor chip 10 is modified with primary antibody $B_1$ as an immobilization layer is prepared. The primary antibody $B_1$ is the first binding substance that specifically binds to the antigen A.

First, liquid sample S, which is an examination object (assay target or examination target), is poured into the sample retaining unit 13 to make the liquid sample S in contact with the metal film 12 of the sensor chip 10. Next, a solution containing fluorescent-label binding substance (labeling secondary antibody) $B_F$ is poured into the sample retaining unit 13 in a similar manner. The fluorescent-label binding substance $B_F$ includes secondary antibody $B_2$, which is a second binding substance that specifically binds to the antigen A, and fluorescent label F. In this case, the primary antibody $B_1$ that is used for surface modification of the metal film 12 and the secondary antibody $B_2$ of the fluorescent-label binding substance $B_F$ are selected so that they bind to different sites of the antigen A, which is the detection target substance. Here, fluorescent substance F that includes fluorescent dye molecules f, and the surface of which is modified with carboxyl group (—COOH), is used as the fluorescent label. The carboxyl group is ionized ($COO^-$) at the vicinity of pH 7.4 in a liquid sample, such as physiologic saline. When the pH of the liquid sample is lowered, $COO^-$ protonates, and changes to COOH. Consequently, the fluorescent substance is electrically neutralized.

When the antigen A is present in the sample S, the antigen A specifically binds to the primary antibody $B_1$, and the secondary antibody $B_2$ in the fluorescent-label binding substance $B_F$ binds to the antigen A. Consequently, a bound body of (primary antibody $B_1$)-(antigen A)-(secondary antibody $B_2$) (hereinafter, referred to as a sandwich bound body) is formed.

After then, a buffer solution (buffer) is poured to separate the sandwich bound body from unreacted fluorescent-label binding substance $B_F$. Consequently, the unreacted fluorescent-label binding substance $B_F$ is eliminated.

Further, the timing of labeling the detection target substance (antigen A) is not particularly limited. A fluorescent label may be added to the sample in advance before the detection target substance (antigen A) binds to the first binding substance (primary antibody $B_1$).

After then, with the sensor chip 10 set in the housing unit 19, the pH adjustment means 35 dispenses the pH adjustment liquid into the sample cell to adjust the pH of the liquid sample. Specifically, an acetic acid buffer solution is injected to lower the pH to the vicinity of pH 5, and desirably to the vicinity of approximately pH 4.5. Accordingly, $COO^-$ on the surface of the fluorescent substance F of the fluorescent-label binding substance $B_F$ that has bound to the sensor portion protonates, and changes to COOH. Consequently, the fluorescent substance F is electrically neutralized, and attracted to the sensor portion 14. In the state in which the fluorescent substance F is attracted to the sensor portion 14 as described above, excitation light $L_0$ is output to a predetermined area of the dielectric plate 11 of the sensor chip 10 from the excitation light irradiation optical system 20. The excitation light irradiation optical system 20 outputs the excitation light $L_0$ in such a manner that the excitation light $L_0$ enters the interface between the dielectric plate 11 and the metal layer 12 at a specific incident angle that is greater than or equal to a total reflection angle. When the light $L_0$ enters the interface in such a manner, evanescent waves extend to the sample S on the metal layer 12, and surface plasmons are excited in the metal layer 12 by the evanescent waves. Further, the optical field (an electric field induced by evanescent waves) that has been generated on the metal layer by the incident excitation light is enhanced by the surface plasmons. Accordingly, optical field enhanced region D is formed on the metal layer. Since the fluorescent substance F has been attracted to the surface of the metal layer in the optical field enhanced region D, the fluorescent substance F is excited (fluorescent dye molecules f in the fluorescent substance are substantially excited), and fluorescence $L_f$ is output. The fluorescence is enhanced by the optical field enhancement effect by the surface plasmons. The fluorescence $L_f$ is detected by the photodetector 30. Therefore, it is possible to detect the presence and/or amount of the detection target substance that has bound to the fluorescent-label binding substance by detecting fluorescence at the photodetector 30.

As described above, the pH of the liquid sample is adjusted, and the charge state of the fluorescent substance (the charge state of the functional group that modifies the surface of the fluorescent substance) is neutralized to attract the fluorescent substance to the sensor portion. Further, fluorescence is detected in the state in which the fluorescent substance has been attracted to the sensor portion. Hence, it is possible to obtain stable signals at an excellent S/N ratio. Further, it is possible to improve the reliability of examination.

<Design Modification Example of First Embodiment>

Figure 3:
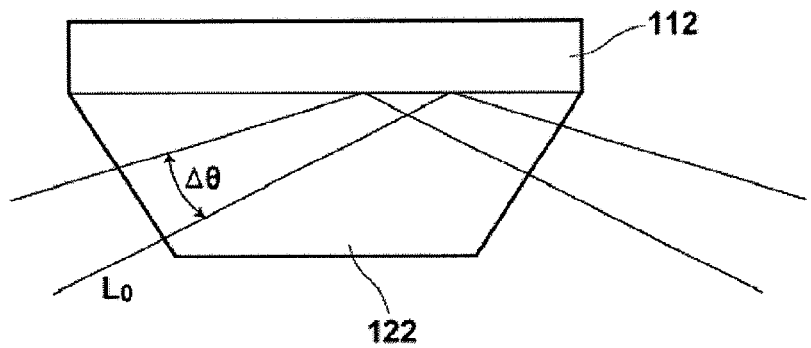
FIG. 3 is a diagram illustrating a design modification example of an excitation light irradiation optical system.

In each of the aforementioned examples, the excitation light $L_0$ is collimated light that enters the interface at predetermined angle θ. Alternatively, the excitation light may be a fan beam (condensed light), as schematically illustrated in FIG. 3, which has angle width Δθ with respect to angle θ. When the excitation light is a fan beam, the excitation light enters the interface between the prism 122 and the metal film 112 on the prism 122 at an incident angle within the range of θ−Δθ/2 to θ+Δθ/2. When a resonance angle is present in the range of angles, it is possible to excite surface plasmons in the metal film 112. Further, the refractive index of the medium changes when the sample is supplied onto the metal film. In other words, the refractive index of the medium before supply of the sample and the refractive index of the medium after supply of the sample differ from each other. Therefore, the resonance angle at which surface plasmons are generated changes. When the collimated light is used as the excitation light as in the aforementioned examples, it is necessary to adjust the incident angle of the collimated light every time when the resonance angle changes. However, when the fan beam, as illustrated in FIG. 3, the incident angle of which has a certain width, is used, it is possible to cope with the change in the resonance angle without adjusting the incident angle. Further, it is desirable that the fan beam has flat distribution, in which a change in the intensity of light according to the incident angle is small.

Second Embodiment

A detection method and apparatus according to a second embodiment will be described with reference to FIG. 4. FIG. 4 is a schematic diagram illustrating the structure of the whole detection apparatus of the second embodiment. The detection method and apparatus in this embodiment enhances an optical field by localized plasmon resonance, and detects fluorescence excited in the enhanced optical field. In the following descriptions, the same reference numerals will be assigned to elements corresponding to the elements in the first embodiment.

In a fluorescence detection apparatus 2 illustrated in FIG. 4, a sensor chip 10' and an excitation light irradiation optical system 20' differ from the elements of the fluorescence detection apparatus 1 of the first embodiment.

The sensor chip 10' includes, as a metal layer 12' provided on the dielectric plate 11, a metal fine structure body or a plurality of metal nanorods, which generate so-called localized plasmons by irradiation with the excitation light. The metal fine structure body includes an uneven structure (an uneven pattern, or projections/depressions) that is smaller than the wavelength of the excitation light $L_0$. Further, the size of each of the plurality of metal nanorods is smaller than the wavelength of the excitation light $L_0$. When the metal layer 12' as described above, which generates localized plasmons, is provided, it is not necessary that the excitation light enters the interface between the metal layer 12' and the dielectric plate 11 at a total reflection angle. Therefore, an excitation light irradiation optical system 20' is arranged in such a manner that the excitation light $L_0$ is output to the sensor chip 10' from the upper side of the dielectric plate 11.

The excitation light irradiation optical system 20' includes a light source 21, such as a semiconductor laser (LD), and a half mirror 23. The light source 21 outputs the excitation light $L_0$, and the half mirror 23 reflects the excitation light $L_0$, and guides the excitation light $L_0$ to the sensor chip 10'. The half mirror 23 reflects the excitation light $L_0$, and transmits fluorescence $L_f$.

A specific example of the sensor chip 10' will be described with reference to perspective views illustrated in FIGS. 5A through 5C.

Figure 5A:
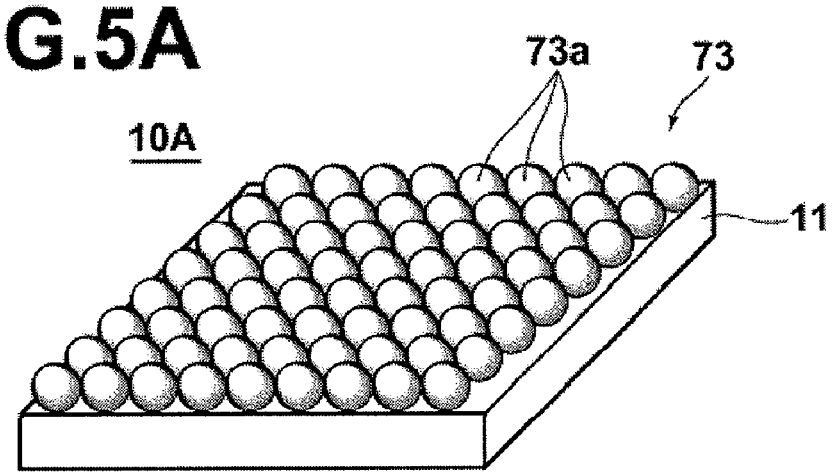
FIG. 5A is a schematic diagram illustrating the structure of a sensor portion of a sensor chip used in a fluorescence detection apparatus 2 (No. 1)

A sensor chip 10A illustrated in FIG. 5A includes the dielectric plate 11 and a metal fine structure body 73. The metal fine structure body 73 includes a plurality of metal particles 73a fixed in array form on a predetermined area of the dielectric plate 11. The arrangement pattern of the metal particles 73a may be appropriately designed, and it is desirable that the arrangement pattern is substantially regular. This structure is designed in such a manner that an average particle diameter of the metal particles 73a and an average pitch thereof are smaller than the wavelength of the excitation light $L_0$.

Figure 5B:
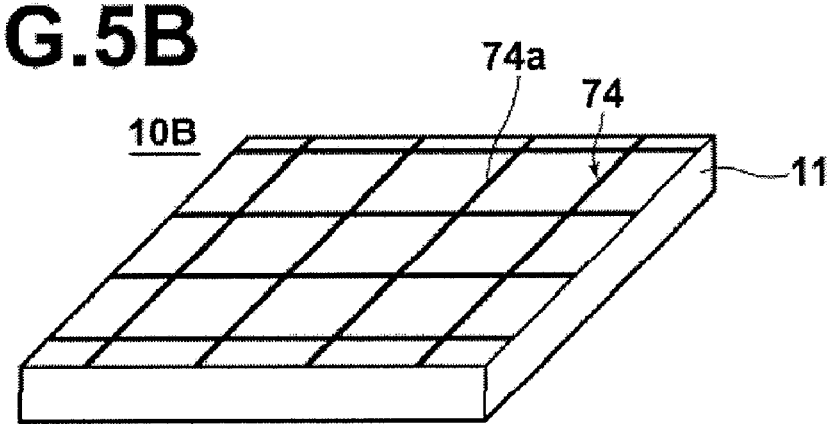
FIG. 5B is a schematic diagram illustrating the structure of a sensor portion of a sensor chip used in the fluorescence detection apparatus 2 (No. 2)

A sensor chip 10B illustrated in FIG. 5B includes the dielectric plate 11 and a metal fine structure body 74 provided on a predetermined area of the dielectric plate 11. The metal fine structure body 74 is formed by a metal pattern layer. In the metal pattern layer, metal thin wires 74a are arranged in grid form by pattern formation. The pattern of the metal pattern layer may be appropriately designed, and it is desirable that the pattern is substantially regular. This structure is designed in such a manner that an average width (line width) of the metal thin wires 74a and an average pitch thereof are smaller than the wavelength of the excitation light $L_0$.

Figure 5C:
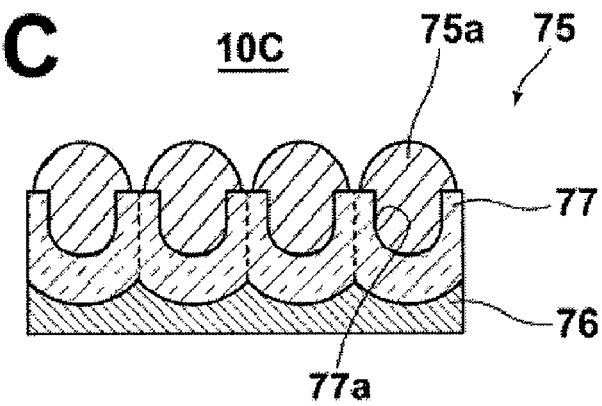
FIG. 5C is a schematic diagram illustrating the structure of a sensor portion of a sensor chip used in the fluorescence detection apparatus 2 (No. 3)

A sensor chip 10C illustrated in FIG. 5C includes a metal fine structure body 75 as disclosed in U.S. Patent Application Publication No. 20070158549. The metal fine structure body 75 includes a plurality of mushroom-shape metals 75a that have grown in a plurality of minute pores (holes) 77a in a metal oxide object 77. The minute pores 77a are formed in the process of anodic oxidation of a metal 76, such as Al. Here, the metal oxide object 77 corresponds to the dielectric plate 11. The metal fine structure body 75 can be produced by obtaining a metal oxide object ($Al_2O_3$ or the like) by performing anodic oxidation on a part of a metal body (Al or the like) and by making the metal 75a grow in each of the plurality of minute pores 77a in the metal oxide object 77 by plating or the like. The plurality of minute pores 77a are formed in the process of anodic oxidation.

In the example illustrated in FIG. 5C, the top portion of the mushroom-shape metal 75a has particle form. Therefore, when the metal fine structure body 75 is observed from the surface of the sample plate, the metal fine structure body 75 is structured in such a manner that metal microparticles are arranged. In this structure, the top portions of the mushroom-shape metals 75a are projections (projections in an uneven pattern), and the structure is designed in such a manner that an average diameter of the projections (top portions) and an average pitch thereof are smaller than the wavelength of excitation light $L_0$.

Further, as the metal layer 12', which generates localized plasmons by irradiation with excitation light, various kinds of other metal fine structure bodies may be used. The various kinds of metal fine structure bodies utilize fine structures obtained by performing anodic oxidation on metal bodies, as disclosed in U.S. Patent Application Publication No. 20060234396, U.S. Patent Application Publication No. 20060181701, and the like.

Further, the metal layer that generates localized plasmons may be formed by a metal film (coating) the surface of which has been coarsened. As a method for coarsening the surface, there is an electro-chemical method utilizing oxidation/reduction or the like. Further, the metal layer may include a plurality of metal nanorods arranged on a sample plate. The short-axial length of the metal nanorods is approximately 3 nm to 50 nm, and the long-axial length of the metal nanorods is approximately 25 nm to 1000 nm. Further, the long-axial length should be less than the wavelength of the excitation light. The metal nanorods are disclosed, for example, in U.S. Patent Application Publication No. 20070118936, or the like.

Further, it is desirable that the metal fine structure body and the metal nanorods, which are used as the metal layer 12', contain, as a main component, at least one kind of metal selected from the group consisting of Au, Ag, Cu, Al, Pt, Ni, Ti and alloys thereof.

Next, a fluorescence detection method of the present embodiment using the fluorescence detection apparatus 2 will be described.

The processes of preparing a sensor chip, causing antigen-antibody reaction, and attracting the fluorescent substance onto the sensor portion are similar to the processes in the first embodiment. Therefore, the explanation about these processes will be omitted in the following embodiments.

In a state in which the fluorescent substance F is attracted to the sensor portion 14, excitation light $L_0$ is output to a predetermined area on the dielectric plate 11 of the sensor chip 10' from the excitation light irradiation optical system 20'. The excitation light $L_0$ output from the light source 21 is reflected by a half mirror 23, and enters the sample-contact surface of the sensor chip 10'. Consequently, localized plasmons are excited on the surface of the metal layer 12' by irradiation with the excitation light $L_0$. Further, the optical field (an electric field induced by near field light) that has been generated on the metal layer by the incident excitation light is enhanced by the localized plasmons. Accordingly, optical field enhanced region D is formed on the metal layer. Since the fluorescent substance F has been attracted to the surface of the metal layer in the optical field enhanced region D, the fluorescent substance F is excited (fluorescent dye molecules f in the fluorescent substance are substantially excited), and fluorescence $L_f$ is output. The fluorescence is enhanced by the optical field enhancement effect by the localized plasmons. The fluorescence $L_f$ is detected by the photodetector 30. Therefore, it is possible to detect the presence and/or amount of the detection target substance that has bound to the fluorescent-label binding substance by detecting fluorescence at the photodetector 30.

In the present embodiment, the pH of the liquid sample is adjusted, and the charge state of the fluorescent substance (the charge state of the functional group that modifies the surface of the fluorescent substance) is neutralized to attract the fluorescent substance to the sensor portion. Further, fluorescence is detected in the state in which the fluorescent substance has been attracted to the sensor portion. Therefore, it is possible to achieve an advantageous effect similar to the first embodiment.

Third Embodiment

A detection method and apparatus according to a third embodiment will be described with reference to FIG. 6. FIG. 6 is a schematic diagram illustrating the structure of the detection apparatus of the third embodiment. The detection method and apparatus in this embodiment enhances an electric field by surface plasmon resonance, and fluorescence excited in the enhanced electric field newly induces plasmons in the metal layer. Further, light from the newly-induced plasmons radiates from the opposite surface of the dielectric plate, the opposite surface being opposite to the metal-layer-formation surface of the dielectric plate. Further, radiation light from the newly induced plasmons is detected in the radiation light detection method and apparatus of this embodiment.

In a radiation light detection apparatus 3, illustrated in FIG. 6, the arrangement of the photodetector is different from the arrangement of the photodetector in the fluorescence detection apparatus of the first embodiment. In the radiation light detection apparatus 3 of the present embodiment, the photodetector 30 is arranged in such a manner that radiation light $L_p$ from the newly induced plasmons is detected. The plasmons are newly induced in the metal layer by fluorescence, and the radiation light $L_p$ from the newly induced plasmons radiates from the opposite surface of the dielectric plate, the opposite surface being opposite to the metal layer formation surface of the dielectric plate.

A radiation light detection method of the present embodiment using the radiation light detection apparatus 3 will be described.

In a state in which the fluorescent substance F is attracted to the sensor portion 14, excitation light $L_0$ is output from the excitation light irradiation optical system 20 in a manner similar to the first embodiment. The excitation light irradiation optical system 20 outputs the excitation light $L_0$ in such a manner that the excitation light $L_0$ enters the interface between the dielectric plate 11 and the metal layer 12 at a specific incident angle that is greater than or equal to a total reflection angle. When the light $L_0$ enters the interface in such a manner, evanescent waves extend to the sample S on the metal layer 12, and surface plasmons are excited in the metal layer 12 by the evanescent waves. Further, the optical field (an electric field induced by evanescent waves) that has been generated on the metal layer by the incident excitation light is enhanced by the surface plasmons. Accordingly, optical field enhanced region D is formed on the metal layer. Since the fluorescent substance F has been attracted to the surface of the metal layer in the optical field enhanced region D, the fluorescent substance F is excited (fluorescent dye molecules f in the fluorescent substance are substantially excited), and fluorescence $L_f$ is output. The fluorescence is enhanced by the optical field enhancement effect by the surface plasmons. The fluorescence $L_f$ generated on the metal film 12 newly induces surface plasmons in the metal film 12, and radiation light $L_p$ is output by the surface plasmons at a specific angle from an opposite surface of the sensor chip 10, the opposite surface being opposite to the metal film formation surface of the sensor chip 10. Further, the radiation light $L_p$ is detected by the photodetector 30. Accordingly, it is possible to detect the presence and/or amount of the detection target substance that has bound to the fluorescent-label binding substance.

The radiation light $L_p$ is generated when fluorescence couples to surface plasmons of a specific wavenumber in the metal film. The wavenumber of the surface plasmons that couple to the fluorescence is determined by the wavelength of the fluorescence. Further, the output angle of radiation light is determined by the wavenumber. Ordinarily, the wavelength of excitation light $L_0$ and the wavelength of fluorescence differ from each other. Therefore, the wavenumber of the surface plasmons excited by the fluorescence differs from that of the surface plasmons generated by the excitation light $L_0$. Therefore, the radiation light $L_p$ is output at an angle different from the incident angle of the excitation light $L_0$.

In the present embodiment, the pH of the liquid sample is adjusted, and the charge state of the fluorescent substance (the charge state of the functional group that modifies the surface of the fluorescent substance) is neutralized to attract the fluorescent substance to the sensor portion. Further, fluorescence is generated in the state in which the fluorescent substance is attracted to the sensor portion, and radiation light induced by the enhanced fluorescence is detected. Therefore, it is possible to achieve an advantageous effect similar to the first embodiment.

Further, in the present embodiment, light caused by the fluorescence generated on the surface (front surface) of the sensor is detected from the back side of the sensor. Therefore, it is possible to reduce the distance of a solvent through which the fluorescence $L_f$ passes (travels), and which greatly absorbs light, to approximately several tens nm. Therefore, it is possible to substantially ignore light absorption, for example, in blood. Therefore, it is possible to perform measurement without performing pre-processing, such as centrifuging the blood to remove a colored component, such as red blood cells, from the blood, and filtering the blood through a blood cell filter to obtain blood serum or blood plasma.

Fourth Embodiment

A detection method and apparatus according to a fourth embodiment will be described with reference to FIG. 7. FIG. 7 is a schematic diagram illustrating the structure of the whole detection apparatus of the fourth embodiment. The detection method and apparatus in this embodiment uses a sensor chip including an optical waveguide layer on the metal layer, and excites an optical waveguide mode in the optical waveguide layer by irradiation with excitation light. Further, an optical field is enhanced by the optical waveguide mode, and fluorescence is excited in the enhanced optical field to detect the fluorescence.

The structure of the fluorescence detection apparatus 4 illustrated in FIG. 7 is the same as the structure of the fluorescence detection apparatus of the first embodiment. However, the sensor chip used in the present embodiment differs from the sensor chip used in the first embodiment. The mechanism of enhancing the optical field in the present embodiment differs because of the difference in the sensor chip.

A sensor chip 10″ includes an optical waveguide layer 12b on the metal layer 12a. The thickness of the optical waveguide layer 12b is not particularly limited. The thickness of the optical waveguide layer 12b may be determined so that the optical waveguide mode is induced. The thickness is determined by considering the wavelength of the excitation light $L_0$, the incident angle of the excitation light $L_0$, the refractive index of the optical waveguide layer 12b, and the like. For example, when a laser beam that has a center wavelength of 780 nm is used as the excitation light $L_0$ in a manner similar to the aforementioned example, and the optical waveguide layer 12b made of a single layer of silicon oxide film is used, it is desirable that the thickness of the optical waveguide layer 12b is approximately in the range of 500 to 600 nm. Further, the optical waveguide layer 12b may have layered structure including at least a layer of internal optical waveguide layer made of an optical waveguide material, such as a dielectric. It is desirable that the layered structure is an alternately-layered structure in which an internal optical guide layer and an internal metal layer are sequentially deposited from the metal layer side.

A fluorescence detection method according to the present embodiment using the fluorescence detection apparatus 4 will be described.

In a state in which the fluorescent substance F is attracted to the sensor portion 14, excitation light $L_0$ is output from the excitation light irradiation optical system 20 in a manner similar to the first embodiment. The excitation light irradiation optical system 20 outputs the excitation light $L_0$ in such a manner that the excitation light $L_0$ enters the interface between the dielectric plate 11 and the metal layer 12 at a specific incident angle that is greater than or equal to a total reflection angle. When the light $L_0$ enters the interface in such a manner, evanescent waves extend to the optical waveguide layer 12b on the metal layer 12, and the evanescent waves couple to the optical waveguide mode of the optical waveguide layer 12b. Accordingly, an optical waveguide mode is excited. Further, the optical field (an electric field induced by evanescent waves) that has been generated on the metal layer by the incident excitation light is enhanced by the optical waveguide mode. Accordingly, optical field enhanced region D is formed on the optical waveguide layer. Since the fluorescent substance F has been attracted to the surface of the metal layer in the optical field enhanced region D, the fluorescent substance F is excited (fluorescent dye molecules f in the fluorescent substance are substantially excited), and fluorescence $L_f$ is output. The fluorescence is enhanced by the optical field enhancement effect by the optical waveguide mode. The fluorescence $L_f$ is detected by the photodetector 30. Accordingly, it is possible to detect the presence and/or amount of the detection target substance that has bound to the fluorescent-label binding substance.

In the present embodiment, the pH of the liquid sample is adjusted, and the charge state of the fluorescent substance (the charge state of the functional group that modifies the surface of the fluorescent substance) is neutralized to attract the fluorescent substance to the sensor portion. Further, fluorescence is generated in the state in which the fluorescent substance is attracted to the sensor portion, and radiation light induced by the enhanced fluorescence is detected. Therefore, it is possible to achieve an advantageous effect similar to the first embodiment.

Further, in the distribution of optical field enhanced by excitation of the optical waveguide mode, the degree of attenuation of the electric field according to the distance from the surface is small, compared with the degree of attenuation in the distribution of optical field generated by surface plasmons. Therefore, when a fluorescent substance that has a large diameter, and which includes a plurality of fluorescent dye molecules, is used as the fluorescent substance of the fluorescent label, a greater fluorescent amount increase effect is achieved in enhancement of the optical field by the optical waveguide mode, compared with enhancement of the optical field by surface plasmons.

Fifth Embodiment

A detection method and apparatus according to a fifth embodiment will be described with reference to FIG. 8. FIG. 8 is a schematic diagram illustrating the structure of the whole detection apparatus of the fifth embodiment. The detection method and apparatus of this embodiment uses a sensor chip including an optical waveguide layer on the metal layer, and excites an optical waveguide mode in the optical waveguide layer by irradiation with excitation light. Further, an optical field is enhanced by the optical waveguide mode, and fluorescence excited in the enhanced optical field newly induces plasmons in the metal layer. Further, light from the newly-induced plasmons radiates from the opposite surface of the dielectric plate, the opposite surface being opposite to the metal-layer-formation surface of the dielectric plate. Further, radiation light from the newly induced plasmons is detected in the radiation light detection method and apparatus of this embodiment.

The structure of the radiation light detection apparatus 5 illustrated in FIG. 8 is similar to the radiation light detection apparatus of the third embodiment. The sensor chip used in the detection method of the present embodiment is similar to the sensor chip used in the fluorescence detection method of the fourth embodiment.

A radiation detection method according to the present embodiment using the radiation light detection apparatus 5 will be described.

In a state in which the fluorescent substance F is attracted to the sensor portion 14, excitation light $L_0$ is output from the excitation light irradiation optical system 20 in a manner similar to the first embodiment. The excitation light irradiation optical system 20 outputs the excitation light $L_0$ in such a manner that the excitation light $L_0$ enters the interface between the dielectric plate 11 and the metal layer 12 at a specific incident angle that is greater than or equal to a total reflection angle. When the light $L_0$ enters the interface in such a manner, evanescent waves extend to the optical guide layer 12b on the metal layer 12, and the evanescent waves couple to the optical waveguide mode of the optical waveguide layer 12b. Accordingly, an optical waveguide mode is excited. Further, the optical field (an electric field induced by evanescent waves) that has been generated on the optical waveguide layer by the incident excitation light is enhanced by the optical waveguide mode. Accordingly, optical field enhanced region D is formed on the optical waveguide layer. Since the fluorescent substance F has been attracted to the surface of the metal layer in the optical field enhanced region D, the fluorescent substance F is excited (fluorescent dye molecules f in the fluorescent substance are substantially excited), and fluorescence $L_f$ is output. The fluorescence is enhanced by the optical field enhancement effect by the optical waveguide mode. The fluorescence $L_f$ generated on the optical waveguide layer 12b newly induces surface plasmons in the metal film 12, and radiation light $L_p$ is output by the surface plasmons at a specific angle from an opposite surface of the sensor chip 10, the opposite surface being opposite to the metal film formation surface. Further, the radiation light $L_p$ is detected by the photodetector 30. Accordingly, it is possible to detect the presence and/or amount of the detection target substance labeled with the fluorescent label F.

In the present embodiment, the pH of the liquid sample is adjusted to neutralize the charge state of the fluorescent substance (the charge state of a functional group that modifies the surface of the fluorescent substance). Therefore, fluorescence is generated in a state in which the fluorescent substance is attracted to the sensor portion. Further, radiation light induced by the enhanced fluorescence is detected. Therefore, it is possible to achieve an advantageous effect similar to the first embodiment.

Further, in the present embodiment, light induced by the fluorescence generated on the surface (front surface) of the sensor is detected from the back side of the sensor. Therefore, it is possible to reduce the distance of a solvent through which the fluorescence $L_f$ passes, and which greatly absorbs light, to approximately several tens nm. Hence, it is possible to achieve an effect similar to the second embodiment.

Further, since the electric field enhancement by excitation of the optical waveguide mode is used, it is possible to achieve a fluorescent amount increase effect similar to the fourth embodiment.

Figure 9:
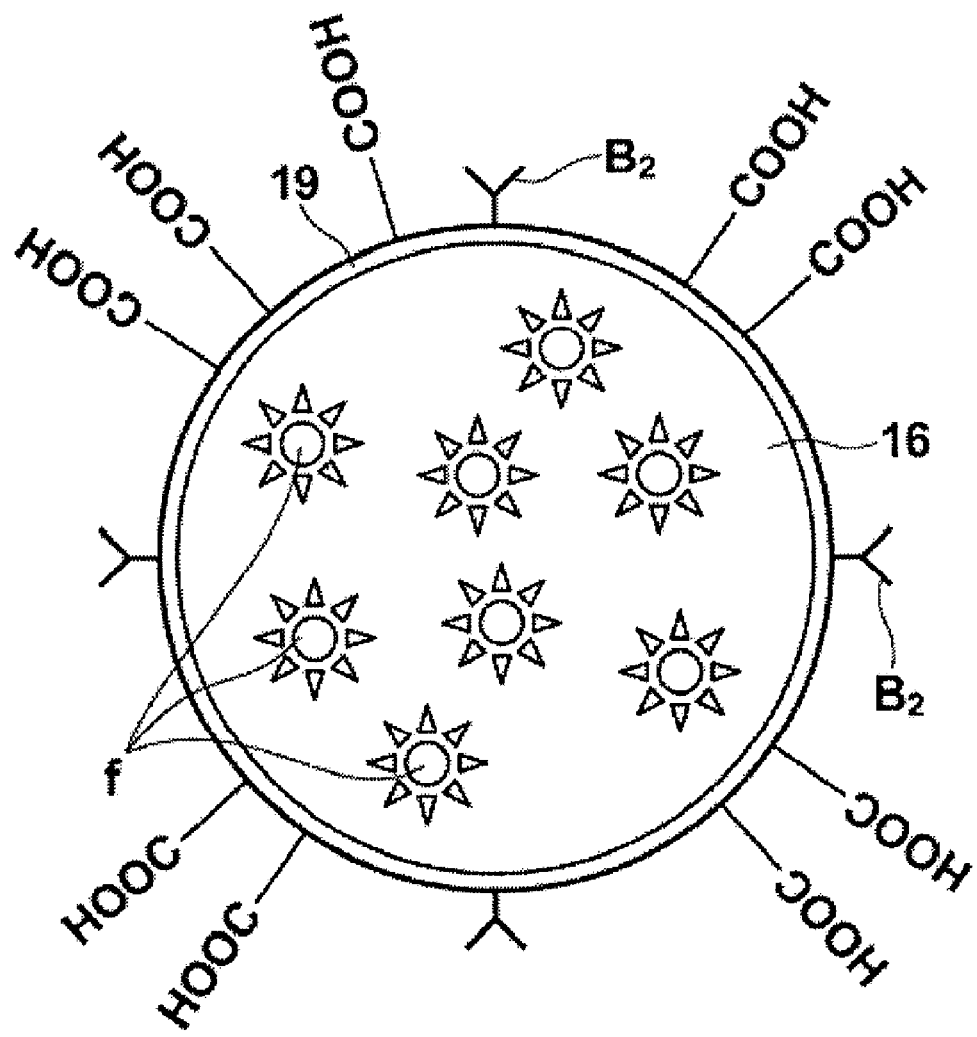
FIG. 9 is a schematic diagram illustrating a fluorescent substance having a metal coating.

Further, in the method of the present invention, as illustrated in FIG. 9, a metal coating 19 may be further provided on the surface of the material 16. The thickness of the metal coating 19 should be sufficiently thin to transmit fluorescence. The metal coating 19 may be provided on the entire surface of the material 16. Alternatively, the metal coating 19 may be provided in such a manner that a part of the surface of the material 16 is exposed. As the material of the metal coating 19, a metal material similar to the aforementioned material of the metal layer may be used.

When the metal coating 19 is provided on the surface of the fluorescent substance, the surface plasmons or localized plasmons generated in the metal layers 12, 12' of the sensor chips 10, 10' couple to a whispering gallery mode of the metal coating 19 of the fluorescent substance F. Therefore, it is possible to more efficiently excite the fluorescent dye molecules f in the fluorescent substance F. The whispering gallery mode is an electromagnetic wave mode that is localized on the spherical surface of a micro-sphere of approximately ($\phi$5300 nm or less, such as the fluorescent substance used here, and that travels around the spherical surface of the micro-sphere.

An example of a method for applying the metal coating to the fluorescent substance will be described.

First, a fluorescent substance is produced through the aforementioned procedure. Further, the surface of the fluorescent substance is modified with polyethyleneimine (PEI) (EPOMIN, produced by NIPPON SHOKUBAI CO., LTD).

Next, Pd nano particles having a diameter of 15 nm (average particle diameter of 19 nm, produced by TOKURIKI-HONTEN) is adsorbed by the PEI on the surface of the particle.

The polystyrene particle that has adsorbed the Pd nano particles is impregnated in electroless gold plating solution ($HAuCl_4$, produced by Kojima Chemicals, Co., LTD.). Accordingly, a gold coating is deposited on the surface of the polystyrene particle by electroless plating using Pd nano particles as a catalyst.

"Sample Cell for Detection"

A sample cell for detection that is used as a sensor chip in the detection method of the present invention will be described.

<Sample Cell According to First Embodiment>

Figure 10A:
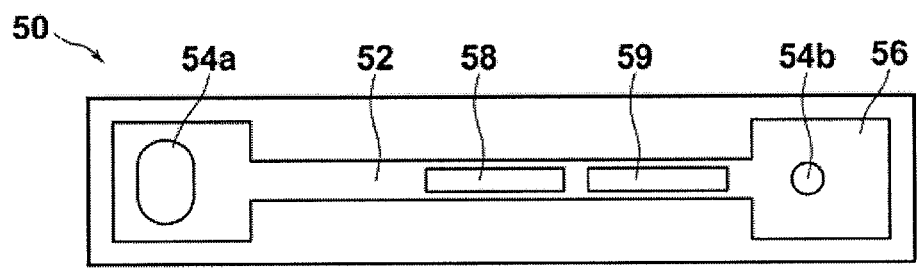
FIG. 10A is a plan view of a sample cell according to the first embodiment of the present invention.
Figure 10B:
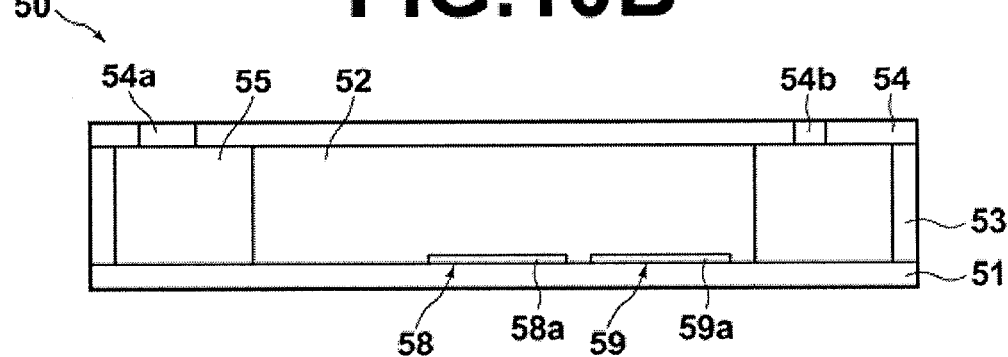
FIG. 10B is a sectional side view of the sample cell according to the first embodiment of the present invention.

FIG. 10A is a plan view illustrating the structure of a sample cell 50 according to a first embodiment. FIG. 10B is a sectional side view of the sample cell 50.

The sample cell 50 for detection includes a base (substrate) 51, a spacer 53, and an upper plate 54. The base 51 is formed by a dielectric plate. The spacer 53 retains liquid sample S on the base 51, and forms a flow path 52 of the liquid sample S. The upper plate 54 is formed by a glass plate that has an injection opening 54a for injecting the sample S and an air hole 54b for discharging the sample that has flowed down through the flow path 52. Further, sensor portions 58, 59 formed by metal layers 58a, 59a are provided in predetermined areas on the sample-contact surface of the base 51. The sensor portions 58, 59 are provided between the injection opening 54a and the air hole 54b of the flow path 52. Further, a membrane filter 55 is provided in a portion of the sample cell 50 from the injection opening 54 to the flow path 52. Further, a waste liquid reservoir 56 is provided on the downstream side of the flow path 52. The waste liquid reservoir 56 is connected to the air hole 54b.

In the present embodiment, the base 51 is formed by the dielectric plate, and the base 51 also functions as the dielectric plate of the sensor portion. Alternatively, only a part of the base, the part constituting the sensor portions, may be formed by the dielectric plate.

The sample cell 50 may be used in any of the detection apparatuses and method in the first through fifth embodiments.

The sample cell 50 for detection of the present invention may be used by appropriately immobilizing, based on the detection target substance, a first binding substance that specifically binds to the detection target substance in the sensor portion.

Further, the sample cell 50 for detection may be used by appropriately immobilizing a fluorescent-label binding substance at a position that is on the upstream side of the sensor portions in the flow path. The fluorescent-label binding substance includes one of a second binding substance that specifically binds to the detection target substance and a third binding substance that competes with the detection target substance and specifically binds to the first binding substance and a fluorescent substance the surface of which is modified with both of the one of the second binding substance and the third binding substance and a functional group that exhibits a polarity at least in the liquid sample.

<Sample Cell According to Second Embodiment>

Figure 11:
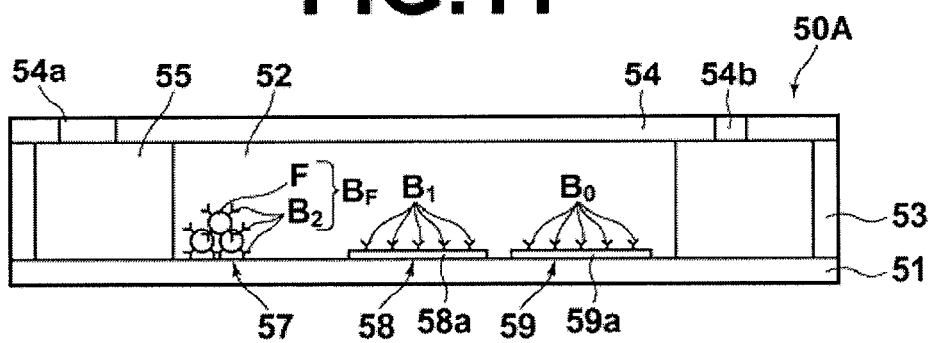
FIG. 11 is a sectional side view of a sample cell according to the second embodiment of the present invention.

FIG. 11 is a sectional side view illustrating a sample cell of the second embodiment that is suitable for an assay by a sandwich method. In a sample cell 50A of the present embodiment, a labeling secondary antibody adsorption area 57, a first measurement area 58, and a second measurement area 59 are sequentially formed on the base 51 from the upstream side of the flow path 52. In the labeling secondary antibody adsorption area 57, a fluorescent-label binding substance $B_F$ (hereinafter, referred to as "labeling secondary antibody $B_F$") has been physically adsorbed. The fluorescent-label binding substance $B_F$ contains the secondary antibody (second binding substance) $B_2$ that specifically binds to the antigen, which is the detection target substance, and fluorescent substance F, the surface of which is modified with both of the secondary antibody $B_2$ and a functional group (for example, —COOH, —NH$_2$ or the like, which is not illustrated) the charge of which changes according to the pH of the liquid sample. In the first measurement area 58, a primary antibody (first binding substance) $B_1$ is immobilized. The primary antibody $B_1$ specifically binds to the antigen, which is the detection target substance. In the second measurement area 59, a primary antibody $B_0$ is immobilized. The primary antibody $B_0$ does not bind to the antigen A, which is the detection target substance, but specifically binds to the labeling secondary antibody $B_F$. The first measurement area 58 and the second measurement area 59 correspond to the sensor portion. In this example, two measurement areas are provided in the sensor portion. Alternatively, only one measurement area may be provided.

In the first measurement area 58, a gold (Au) layer 58a, as a metal layer, is formed on the base 51. In the second measurement area 59, a gold (Au) layer 59a, as a metal layer, is formed on the base 51. Further, primary antibody $B_1$ is immobilized on the Au layer 58a of the first measurement area 58, and primary antibody $B_0$, which is different from the primary antibody $B_1$, is immobilized on the Au layer 59a of the second measurement area 59. The first measurement area 58 and the second measurement area 59 are structured in the same manner except that the immobilized primary antibodies differ from each other. The primary antibody $B_0$, which is immobilized in the second measurement area 59, does not bind to antigen A, but directly binds to secondary antibody $B_2$. Accordingly, it is possible to detect fluctuation factors related to reaction, such as the amount or activity of the labeling secondary antibody $B_F$ that has flowed down in the flow path. Further, it is possible to detect fluctuation factors related to the degree of enhancement of the optical field, such as the excitation light irradiation optical system 20, the gold (Au) layers 58a, 59a, and the liquid sample S. Further, the detected fluctuation factors can be used for calibration. It is not necessary that the primary antibody $B_0$ is immobilized in the second measurement area 59. Instead of the primary antibody $B_0$, a known amount of labeling substance may be immobilized in the second measurement area 59 in advance. The labeling substance may be the same kind of substance as the fluorescent substance F of the labeling secondary antibody $B_F$. Alternatively, the labeling substance may be a fluorescent substance that has a different wavelength and size from the fluorescent substance F of the labeling secondary antibody $B_F$. Further, the labeling substance may be a metal microparticle or the like. In this case, only the fluctuation factors related to the degree of enhancement of optical field, such as the excitation light irradiation optical system 20, the gold (Au) layers 58a, 59a, and the liquid sample S, may be detected to use the detected factors for calibration. Whether the labeling secondary antibody $B_F$ or the known amount of labeling substance that is different from the labeling secondary antibody $B_F$ is immobilized in the second measurement area 59 should be appropriately determined based on the purpose and method of calibration.

The sample cell 50A may be used instead of the sensor chip in any of the detection apparatuses and methods of the first through fifth embodiments in a similar manner. In the housing unit 19, the sample cell 50A can move in X direction relative to the excitation light irradiation optical system 20 and the photodetector 30. After fluorescence or radiation light from the first measurement area 58 is detected and measured, the second measurement area 59 is moved to the detection position, and fluorescence or radiation light from the second measurement area 59 is detected.

Figure 12:
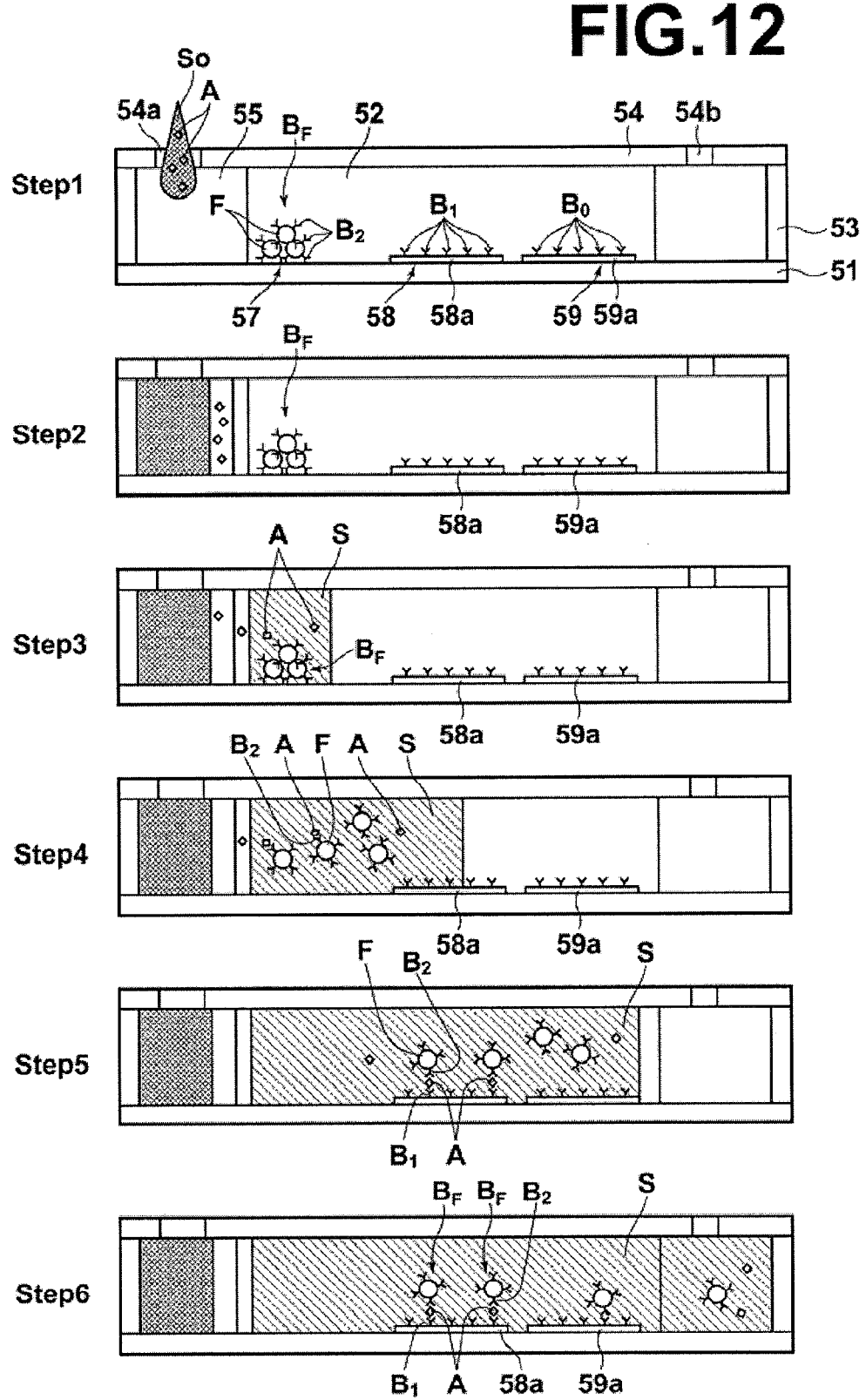
FIG. 12 is a diagram illustrating the procedure of an assay by a sandwich method using the sample cell according to the second embodiment of the present invention.

With reference to FIG. 12, assay procedures by using a sandwich method will be described. In the assay procedures, whether blood (whole blood) contains an antigen, which is a detection target substance, is detected by using the sample cell 50A of the present embodiment.

Step 1: Blood (whole blood) $S_o$, which is the assay target (examination target), is injected from the injection opening 54a. Here, a case in which the antigen that is the detection target substance is included in the blood $S_o$ will be described. In FIG. 12, the whole blood $S_o$ is indicated by a mesh.

Step 2: The whole blood $S_o$ is filtered by the membrane filter 55, and large molecules, such as erythrocyte (red blood cells) and leukocyte (white blood cells), remain as a residue.

Step 3: Blood (plasma, blood plasma) S after blood cells (blood corpuscles) are removed by the membrane filter 55 penetrates into the flow path 52 by a capillary action. Alternatively, a pump may be connected to the air hole 54b to accelerate reaction, thereby reducing detection time. The pump sucks the blood after blood cells are removed by the membrane filter 55 and pumps (pressures to discharge) the sucked blood, thereby causing the blood to flow down through the path. In FIG. 12, the blood plasma S is indicated by a shadow.

Step 4: The blood plasma S that has penetrated into the flow path 52 and the labeling secondary antibody $B_F$ are mixed together. Accordingly, antigen A in the blood plasma and the secondary antibody $B_2$ of labeling secondary antibody $B_F$ bind to each other.

Step 5: The blood plasma S gradually flows down to the air hole 54b side along the flow path 52. The antigen A that has bound to the secondary antibody $B_2$ binds to the primary antibody $B_1$ that has been immobilized in the first measurement area 58. Accordingly, a so-called sandwich is formed, in which the antigen A is sandwiched between the primary antibody $B_1$ and the secondary antibody $B_2$ (labeling secondary antibody $B_F$).

Step 6: A part of the labeling secondary antibody $B_F$ that has not bound to the antigen A binds to the primary antibody $B_0$ immobilized on the second measurement area 59. Further, even if the labeling secondary antibody $B_F$ that has bound neither to the antigen A nor to the primary antibody $B_0$ remains in the measurement areas, the blood plasma flowing next functions as washing liquid, and washes away floating or non-specifically-adsorbed labeling secondary antibody.

As described above, in Steps 1 through 6, the blood is injected from the injection opening and a sandwich in which the antigen A is sandwiched between the primary antibody $B_1$ and the labeling secondary antibody $B_F$ is formed on the measurement area 58. After Steps 1 through 6, the pH adjustment liquid is injected through the injection opening to adjust the pH of the solution in the sample cell so that the functional group that modifies the surface of the fluorescent substance is neutralized. Accordingly, the fluorescent substance is attracted to the sensor portion. Further, in the state in which the fluorescent substance is attracted to the sensor portion, the intensity of fluorescence or radiation light (hereinafter, referred to as "signal") from the first measurement area 58 is detected. After then, the sample cell 50 is moved in X direction so that the signal from the second measurement area 59 can be detected, and the signal from the second measurement area 59 is detected. The signal from the second measurement area 59 in which the primary antibody $B_0$ that binds to the labeling secondary antibody $B_F$ is immobilized reflects reaction conditions, such as the amount and the activity of the labeling secondary antibody that has flowed down. Therefore, if this signal is used as a reference (reference signal) and the signal from the first measurement area is corrected based on the reference, it is possible to obtain a more accurate detection result (presence of the antigen and/or the concentration thereof). Further, even when a known amount of labeling substance (fluorescence substance or metal microparticle) is immobilized in advance in the second measurement area 59, as described above already, it is possible to use the signal from the second measurement area 59 as a reference in a similar manner, and the signal from the first measurement area can be corrected based on the reference.

<Sample Cell According to Third Embodiment>

Figure 13:
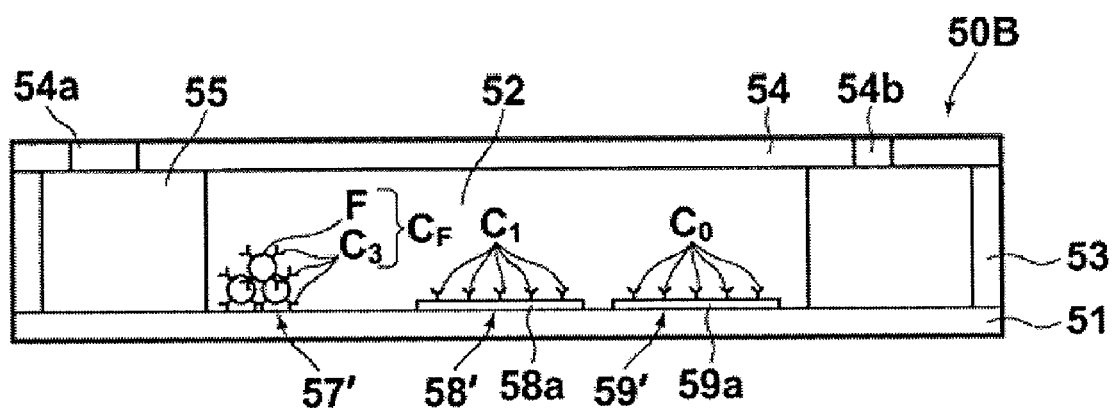
FIG. 13 is a sectional side view illustrating the sample cell according to the third embodiment of the present invention.

FIG. 13 is a sectional side view of a sample cell of the third embodiment that is suitable for an assay by a competition method. In a sample cell 50B of the present embodiment, a labeling secondary antibody adsorption area 57', a first measurement area 58', and a second measurement area 59' are sequentially formed on the base 51 of the sample cell 50B from the upstream side of the flow path 52. In the labeling secondary antibody adsorption area 57', a fluorescent-label binding substance $C_F$ (hereinafter, referred to as "labeling secondary antibody $C_F$") has been physically adsorbed. The fluorescent-label binding substance $C_F$ contains the secondary antibody (third binding substance) $C_3$ that does not bind to the antigen A, which is the detection target substance, and that specifically binds to the primary antibody, which will be described later, and fluorescent substance the surface of which is modified with both of the secondary antibody $C_3$ and a functional group (for example, —COOH, —NH$_2$ or the like, which is not illustrated) the charge state of which changes according to the pH of the liquid sample. In the first measurement area 58', a primary antibody (first binding substance) $C_1$ are immobilized. The primary antibody $C_1$ specifically binds to the antigen A, which is the detection target substance, and the secondary antibody $C_3$. In the second measurement area 59', a primary antibody $C_0$ is immobilized. The primary antibody $C_0$ does not bind to the antigen A, which is the detection target substance, but specifically binds to the secondary antibody $C_3$ of the labeling secondary antibody $C_F$.

In the first measurement area 58', a gold (Au) layer 58a, as a metal layer, is formed on the base 51. In the second measurement area 59', a gold (Au) layer 59a, as a metal layer, is formed on the base 51. Further, primary antibody $C_1$ is immobilized on the Au layer 58a of the first measurement area 58', and primary antibody $C_0$, which is different from the primary antibody $C_1$, is immobilized on the Au layer 59a of the second measurement area 59'. The first measurement area 58' and the second measurement area 59' are structured in the same manner except that the immobilized primary antibodies differ from each other. The antigen A and the secondary antibody $C_3$ compete with each other and bind to the primary antibody $C_1$ that is immobilized in the first measurement area 58'. The primary antibody $C_0$ immobilized in the second measurement area 59' does not bind to antigen A, but directly binds to secondary antibody $C_F$. Accordingly, it is possible to detect fluctuation factors related to reaction, such as the amount and activity of the labeling secondary antibody that has flowed down in the flow path. Further, it is possible to detect fluctuation factors related to the degree of enhancement of the optical field, such as the excitation light irradiation optical system 20, the gold (Au) layers 58a, 59a, and the liquid sample S. Further, the detected fluctuation factors can be used for calibration. It is not necessary that the primary antibody $C_0$ is immobilized in the second measurement area 59'. Instead of the primary antibody $C_0$, a known amount of labeling substance may be immobilized in the second measurement area 59' in advance. The labeling substance may be the same kind of substance as the fluorescent substance F of the labeling secondary antibody $C_F$. Alternatively, the labeling substance may be a fluorescent substance that has a different wavelength and size from the fluorescent substance F of the labeling secondary antibody $C_F$. Alternatively, the labeling substance may be a metal microparticle or the like. In this case, only the fluctuation factors related to the degree of enhancement of the optical field, such as the excitation light irradiation optical system 20, the gold (Au) layers 58a, 59a, and the liquid sample S, may be detected to be used for calibration. Whether the labeling secondary antibody $C_F$ or the known amount of labeling substance, which is different from the labeling secondary antibody $C_F$, is immobilized in the second measurement area 59' may be appropriately determined based on the purpose and method of calibration.

The sample cell 50B may be used instead of the sensor chip in any of the detection apparatuses and methods of the first through fifth embodiments in a manner similar to the sample cell 50A.

Figure 14:
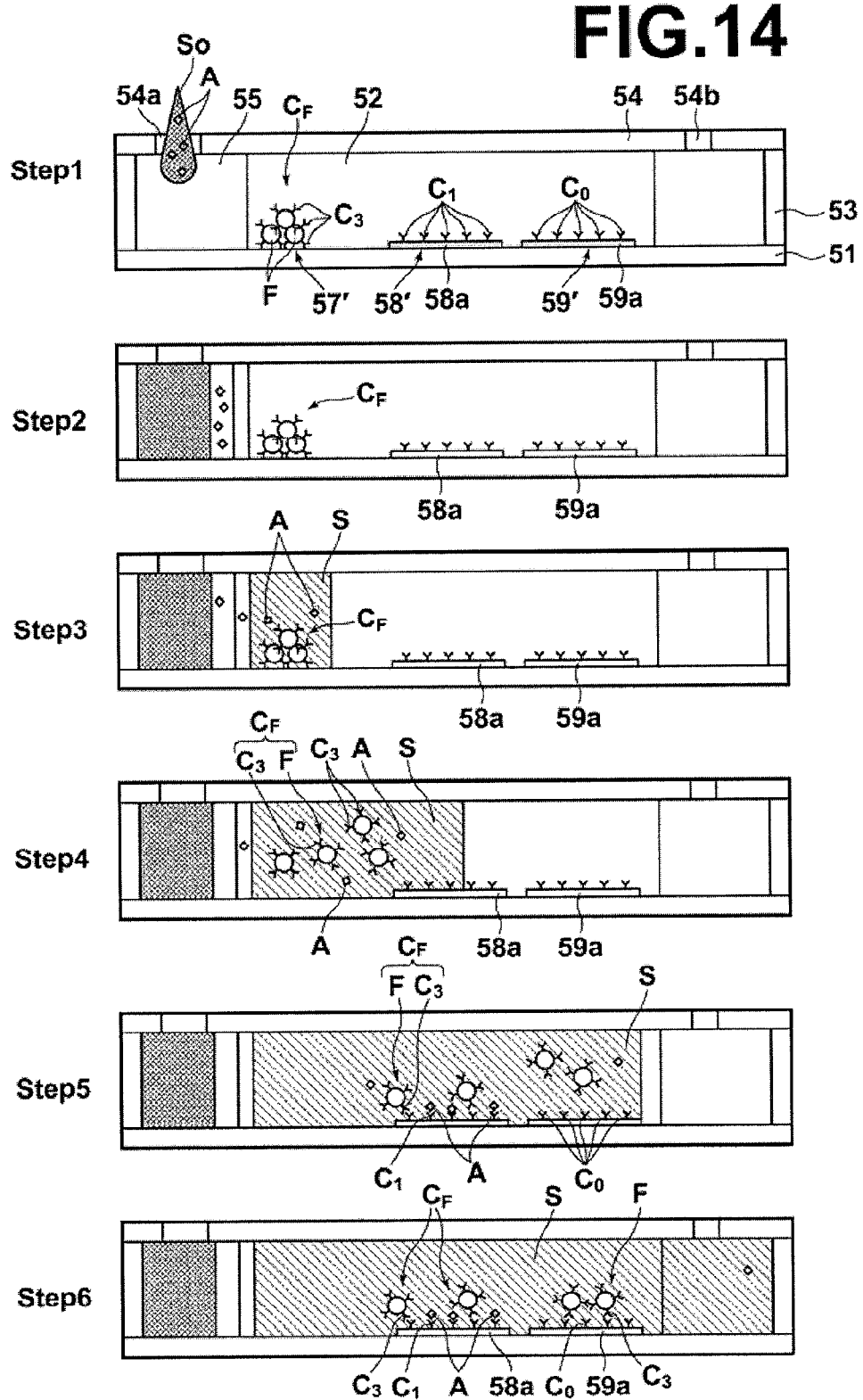
FIG. 14 is a diagram illustrating the procedure of an assay by a competition method using the sample cell according to the third embodiment of the present invention.

With reference to FIG. 14, assay procedures by using a sandwich method will be described. In the assay procedures, the sample cell 50B for detection of the present embodiment is used, and an assay is performed as to whether an antigen, which is a detection target substance, is included in the blood (whole blood).

Step 1: Blood (whole blood) $S_o$, which is the assay target, is injected from an injection opening 54a. Here, a case in which an antigen that is the detection target substance is included in the blood $S_o$ will be described. In FIG. 14, the whole blood $S_o$ is indicated by a mesh.

Step 2: The whole blood $S_o$ is filtered by a membrane filter 55, and large molecules, such as erythrocyte (red blood cells) and leukocyte (white blood cells), remain as the residue.

Step 3: The blood (plasma, blood plasma) S after blood cells are removed by the membrane filter 55 penetrates into the flow path 52 by a capillary action. Alternatively, a pump may be connected to the air hole 54b to accelerate reaction, thereby reducing detection time. The pump sucks the blood after blood cells are removed by the membrane filter 55 and pumps the sucked blood, thereby causing the blood to flow down in the path. In FIG. 14, the blood plasma S is indicated by a shadow.

Step 4: The blood plasma S that has penetrated into the flow path 52 and the labeling secondary antibody $C_F$ are mixed together.

Step 5: The blood plasma S gradually flows down to the air hole 54b side along the flow path 52. The antigen A and the secondary antibody $C_3$ of the labeling secondary antibody $C_F$ competitively bind to the primary antibody $C_1$ that has been immobilized on the first measurement area 58'.

Step 6: A part of the fluorescence labeling secondary antibody $C_F$ that has not bound to the primary antibody $C_1$ on the first measurement area 58' binds to the primary antibody $C_0$ immobilized on the second measurement area 59'. Further, even if the labeling secondary antibody $C_F$ that has bound neither to the primary antibody $C_1$ nor to the primary antibody $C_0$ remains on the measurement areas, the blood plasma S flowing next functions as washing liquid, and washes away a floating or non-specifically-adsorbed labeling secondary antibody $C_F$.

As described above, in Steps 1 through 6, the blood is injected from the injection opening and the antigen A and the secondary antibody $C_3$ competitively bind to the primary antibody $C_1$ on the first measurement area 58'. After Steps 1 through 6, the pH of the solution in the sample cell is adjusted by injecting the pH adjustment liquid through the injection opening so that the functional group that modifies the surface of the fluorescent substance is neutralized. Accordingly, the fluorescent substance is attracted to the sensor portion. Further, in the state in which the fluorescent substance is attracted to the sensor portion, signals, such as the intensity of the fluorescence or radiation light, from the first measurement area 58' are detected. Then, the sample cell 50B is moved in X direction so that the signal from the second measurement area 59' can be detected, and the signal from the second measurement area 59' is detected. The signal from the second measurement area 59' is used as reference, and the signal from the first measurement area is corrected. Hence, it is possible to obtain an accurate measurement result (presence of antigen and/or the concentration thereof).

In the competition method, when the concentration of the detection target substance A is higher, the amount of the third bonding substance $C_3$ that binds to the first binding substance $C_1$ decreases. Specifically, since the number of particles of the fluorescent substance F on the metal layer becomes smaller, the intensity of fluorescence becomes lower. In contrast, when the concentration of the detection target substance A is lower, the amount of the third bonding substance $C_3$ that binds to the first binding substance $C_1$ increases. Specifically, since the number of particles of the fluorescent substance F on the metal layer becomes larger, the intensity of fluorescence becomes higher. In the competition method, measurement is possible if at least one epitope is present in the detection target substance. Therefore, the competition method is suitable to detect a substance that has low molecular weight.

<Sample Cell According to Fourth Embodiment>

Figure 15:
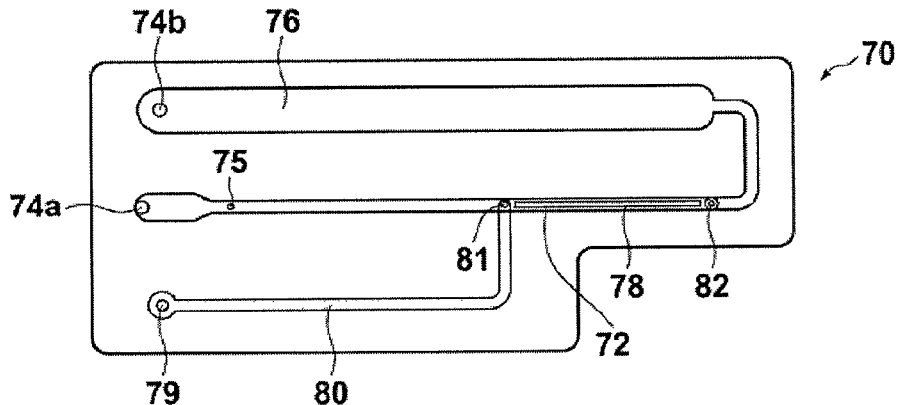
FIG. 15 is a plan view of a sample cell according to the fourth embodiment of the present invention.

FIG. 15 is a plan view illustrating the structure of a sample cell 70 according to the fourth embodiment of the present invention.

The sample cell 70 for detection includes a base (not illustrated), a spacer and an upper plate. The base includes a dielectric plate. The spacer retains liquid sample S on the base, and forms a flow pass 72 of the liquid sample S and a branch path 80, branching from the flow pass 72. The upper plate includes a glass plate having an injection opening 74*a*, an air hole 74*b* and a pH adjustment liquid injection opening 79. The injection opening 74*a* is used to inject the liquid sample S into the sample cell 70, and the air hole 74*b* is a discharge opening for discharging the liquid sample S that has flowed down through the flow path 72. The pH adjustment liquid injection opening 79 is used to inject pH adjustment liquid into the branch path 80. Further, a sensor portion 78 including a metal layer is provided. The metal layer is provided in a predetermined area on a sample-contact surface of the base between the injection opening 74*a* and the air hole 74 in the flow path 72. Further, a membrane filter is provided in a region from the injection opening 74*a* to the flow path 72. Further, a waste liquid reservoir 76 is formed at a downstream portion of the flow path 72 in such a manner to connect to the air hole 74*b*. Further, a switch valve 81 is provided at a branching point between the flow path 72 and the branch path 80 to make it possible to control the order of sending the liquid sample S and the pH adjustment liquid to the sensor portion 78. Further, a valve 82 is provided on the downstream side of the sensor portion. When the fluorescent-label binding substance binds to the sensor portion (by antigen-antibody reaction), the valve 82 is closed to temporarily keep the liquid sample at the sensor portion. After the bond reaction of the fluorescent-label binding substance to the sensor portion ends, when the unreacted fluorescent-label binding substance is washed away, and when the pH of the solution on the sensor portion is adjusted by using the pH adjustment liquid or the like, the valve 82 is opened to make the liquid sample flow down to the waste liquid reservoir 76.

When a sensor chip that includes the pH adjustment liquid injection opening 79 for injecting the pH adjustment liquid, the branch path 80, and the valves 81 and 82 for controlling the order of sending the liquids or adjusting the flow amount of liquid is used, it is possible to easily adjust the pH of the liquid sample on the sensor portion.

The sample cell 70 can be used in any of the detection apparatuses and methods in the first through fifth embodiments of the present invention.

Further, the sample cell 70 for detection may be used by appropriately immobilizing, based on the detection target substance, a first binding substance that specifically binds to the detection target substance in the sensor portion.

Further, a labeling secondary antibody adsorption area 75 may be provided on the upstream side of the sensor portion in the flow path. Specifically, the labeling secondary antibody absorption area 75 may be provided in a flow path between the injection opening 74*a* and the sensor portion 78. In the labeling secondary antibody absorption area 75, a fluorescent-label binding substance including one of a second binding substance that specifically binds to the detection target substance and a third binding substance that competes with the detection target substance and specifically binds to the first binding substance and a fluorescent substance the surface of which is modified with both of the one of the second binding substance and the third binding substance and a functional group that exhibits a polarity in the liquid sample may be appropriately immobilized.

(Design Modification Example of Sample Cell)

Figure 16:
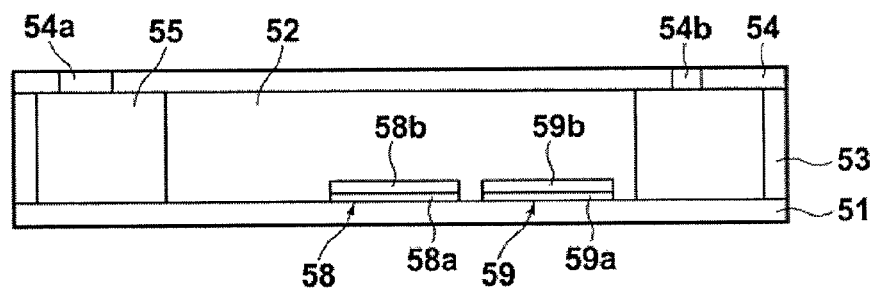
FIG. 16 is a sectional side view illustrating a design modification example of a sample cell.

FIG. 16 is a diagram illustrating a sectional view of a sample cell used in the detection method and apparatus using optical field enhancement by an optical waveguide mode. The structure of the sample cell illustrated in FIG. 16 is substantially the same as the structure of the sample cell of the first embodiment, illustrated in FIGS. 10A and 10B. However, in FIG. 16, optical waveguide layers 58*b*, 59*b* are further provided on the metal layers 58*a*, 59*a* in the sensor portion.

This sample cell may be used by appropriately immobilizing a first binding substance in the sensor portion and a fluorescent-label binding substance on the upstream side of the sensor portion.

"Kit for Detection"

A kit for detection used in the detection method of the present invention will be described.

Figure 17:
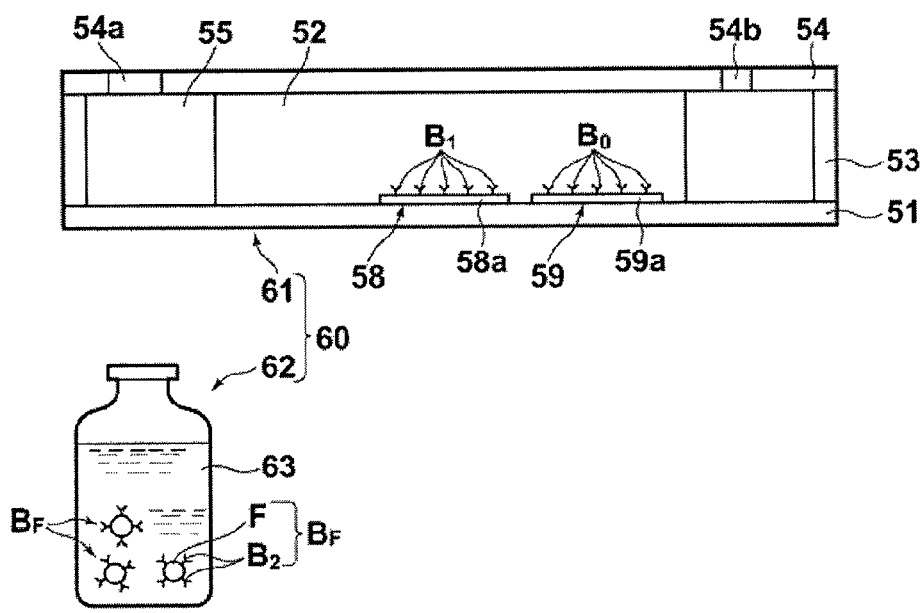
FIG. 17 is a schematic diagram illustrating the structure of a kit for detecting fluorescence according to an embodiment of the present invention.
Figure 18:
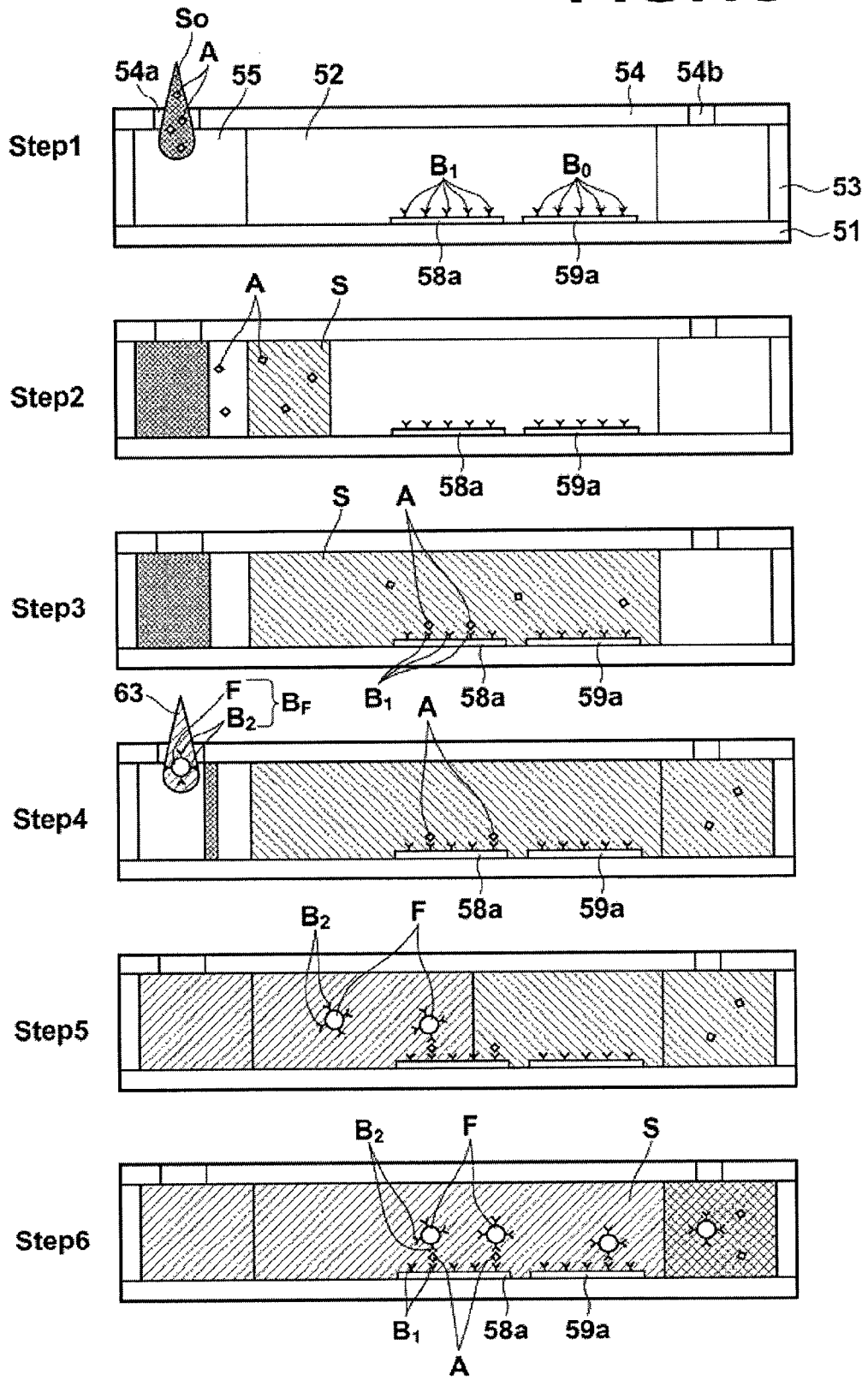
FIG. 18 is a diagram illustrating the procedure of an assay by a sandwich method using the kit for detecting fluorescence.

FIG. 17 is a schematic diagram illustrating the structure of a kit 60 for detecting fluorescence.

The kit 60 for detection includes a sample cell 61 and a solution 63 for labeling, which is injected into the flow path of the sample cell 61 together with the liquid sample or after the liquid sample flows down to perform fluorescence detection measurement. The solution 63 for labeling contains fluorescent-label binding substance $B_F$ (hereinafter, referred to as "labeling secondary antibody $B_F$") containing secondary antibody (second binding substance) $B_2$ that specifically binds to the antigen A and fluorescent substance F the surface of which has been modified with both of the secondary antibody $B_2$ and a functional group (for example, —COOH, —NH$_2$ or the like, which is not illustrated) the charge state of which changes according to the pH of the liquid sample.

The sample cell 61 differs from the sample cell 50A of the second embodiment only in that a physical adsorption area, in which fluorescent-label binding substance $B_F$ is physically adsorbed, is not provided in the sample cell 61. The remaining structure of the sample cell 61 is substantially the same as the structure of the sample cell 50A of the second embodiment.

With reference to FIG. 17, assay procedures in the detection method of the present invention by using a sandwich method will be described. In the assay procedures, the kit 60 for detection of the present embodiment is used, and an assay is performed as to whether the blood (whole blood) contains an antigen, which is the detection target substance.

Step 1: Blood (whole blood) $S_o$, which is the assay target, is injected from an injection opening 54a. Here, a case in which the antigen that is the substance to be detected is contained in the blood $S_o$ will be described. In FIG. 17, the whole blood $S_o$ is indicated by a mesh.

Step 2: The whole blood $S_o$ is filtered by the membrane filter 55, and large molecules, such as erythrocyte (red blood cells) and leukocyte (white blood cells), remain as a residue. Then, the blood (plasma, blood plasma) S after blood cells are removed by the membrane filter 55 penetrates into the flow path 52 by a capillary action. Alternatively, a pump may be connected to the air hole to accelerate reaction, thereby reducing detection time. The pump sucks the blood after blood cells are removed by the membrane filter 55 and pumps the sucked blood, thereby causing the blood to flow down in the path. In FIG. 17, the blood plasma S is indicated by a shadow.

Step 3: The blood plasma S gradually flows to the air hole 54b side along the flow path 52. The antigen A in the blood plasma S binds to the primary antibody $B_1$ that has been immobilized in the first measurement area 58.

Step 4: a solution 63 for labeling is injected from the injection opening 54a. The solution 63 for labeling contains labeling secondary antibody $B_F$.

Step 5: the labeling secondary antibody $B_F$ penetrates into the flow path 52 by a capillary action. Alternatively, a pump may be connected to the air hole to accelerate reaction, thereby reducing detection time. The pump sucks the blood after blood cells are removed by the membrane filter 55 and pumps the sucked blood, thereby causing the blood to flow down in the path.

Step 6: The labeling secondary antibody $B_F$ gradually flows down to the downstream side, and the secondary antibody $B_2$ of the labeling secondary antibody $B_F$ binds to the antigen A. Consequently, a so-called sandwich in which the antigen A is sandwiched between the primary antibody $B_1$ and the secondary antibody $B_2$ is formed. Further, a part of the secondary antibody $B_2$ that has not bound to the antigen A binds to the primary antibody $B_0$ immobilized on the second measurement area 59. Further, even if the labeling secondary antibody $B_F$ that has bound neither to the antigen A nor to the primary antibody $B_0$ remains in the measurement areas, the blood plasma S flowing next functions as washing liquid, and washes away floating or non-specifically-adsorbed labeling secondary antibody on the plate.

As described above, in Steps 1 through 6, the blood is injected from the injection opening and the antigen binds to the primary antibody and the secondary antibody. After Steps 1 through 6, in the detection apparatus, the pH of the solution in the sample cell is adjusted by injecting a pH adjustment liquid through the injection opening so that the functional group that modifies the surface of the fluorescent substance is neutralized. Accordingly, the fluorescent substance is attracted onto the sensor portion. Further, in the state in which the fluorescent substance is attracted onto the sensor portion, a signal from the first measurement area 58 is detected. After then, the sample cell 61 is moved in X direction so that the signal from the second measurement area 59 can be detected. The fluorescent-label binding substance is attracted onto the sensor portion in a similar manner, and the signal from the second measurement area 59 is detected. The signal from the second measurement area 59 in which the primary antibody $B_0$ that binds to the secondary antibody $B_2$ of the labeling secondary antibody $B_F$ is immobilized reflects reaction conditions, such as the amount and activity of the labeling secondary antibody that has flowed down. Therefore, if this signal is used as a reference (reference signal) and the signal from the first measurement area is corrected based on the reference, it is possible to obtain a more accurate detection result (presence of antigen and/or the concentration thereof). Further, a known amount of labeling substance (fluorescent substance or metal microparticle) may be immobilized in advance in the second measurement area 59, and the fluorescence signal from the second measurement area 59 may be used as a reference to correct the signal from the first measurement area 58 based on the reference.

An example of a method for modifying the fluorescent substance with the secondary antibody and an example of a method for producing a solution for labeling will be described.

A solution containing MES buffer of 50 mM and an anti-hCG monoclonal antibody of 5.0 mg/mL (Anti-hCG 5008 SP-5, Medix Biochemica) is added to the fluorescent substance solution (diameter of the fluorescent substance is 500 nm, and the excitation wavelength is 780 nm) that has been prepared as described above, and stirred. Accordingly, the fluorescent substance is modified with the antibody.

Further, a WSC aqueous solution of 400 mg/mL (Product No. 01-62-0011, Wako Pure Chemical Industries, Ltd.) is added, and stirred at a room temperature.

Further, a Glycine aqueous solution of 2 mol/L is added, and stirred. Then, particles are precipitated by centrifugation.

Finally, the supernatant is removed, and PBS (pH 7.4) is added. An ultrasonic wash machine is used to redisperse the fluorescent substance the surface of which has been modified. Further, centrifugation is performed, and the supernatant is removed. Then, 500 μL of PBS (pH 7.4) solution of 1% BSA is added, and the fluorescent substance F is redispersed to obtain a solution for labeling.

(Design Modification Example of Kit for Examination)

As the sample cell that is used in the detection method and apparatus using the optical field enhancement by an optical waveguide mode, the sample cell as illustrated in FIG. 16 may be used. In the sample cell illustrated in FIG. 16, optical waveguide layers 58b, 59b are further provided on the metal layers 58a, 59a of the sensor portion. Further, the primary antibody $B_1$ and the primary antibody $B_0$, which is different from the primary antibody $B_1$, are immobilized on the optical waveguide layers 58b, 59b, respectively.

Further, when an assay by a competition method is performed, instead of the primary antibody $B_1$ and the primary antibody $B_0$, the primary antibody (first binding substance) $C_1$ that specifically binds to the antigen A, which is the detection target substance, and the secondary antibody $C_3$, and the primary antibody $C_0$ that does not bind to the antigen A, which is the detection target substance, but specifically binds to the secondary antibody $C_3$ are immobilized on the sensor portion in the sample cell. Further, as the solution for labeling, a solution containing the fluorescent-label binding substance $C_F$ should be used. The fluorescent-label binding substance $C_F$ contains the secondary antibody (third binding substance) $C_3$ that does not bind to the antigen A, which is the detection target substance, but specifically binds to the primary antibody, and a fluorescent substance, the surface of which is modified with both of the secondary antibody $C_3$ and a functional group the charge state of which changes according to the pH of the liquid sample.

Example

A sample liquid containing a labeling secondary antibody and hCG, as a detection target substance, in physiologic saline (containing NaCl of 150 mM (m mol/L), pH 7.4) was prepared. The labeling secondary antibody included a fluorescent substance the surface of which was modified with both of a secondary antibody and a carboxyl group (—COOH). The secondary antibody included an anti-hCG monoclonal antibody. Further, a sample cell in which a primary antibody including an anti-hCG monoclonal antibody was immobilized, as an immobilization layer, on the metal layer of the sensor portion was prepared. The primary antibody immobilized in the immobilization layer recognizes a site (epitope) of the antigen that is different from a site (epitope) of the antigen recognized by the secondary antibody.

Further, the sample liquid was injected into the sample cell to flow down in the sample cell. Accordingly, a sandwich bound body was formed on the immobilization layer by antigen-antibody reaction. Further, unreacted labeling secondary antibody was washed away with a buffer solution. For all of sample cells, the process till washing away the unreacted labeling secondary antibody was performed in the same manner.

After then, pH adjustment liquid was injected into the sample cell to adjust the pH of the sample liquid in the sample cell. Specifically, a glycine/hydrochloric-acid buffer solution of 10 mM (m mol/L) (10 mM glycine-HCl) was used to adjust the pH of the sample liquid to 3.0. Further, an acetic acid buffer solution of 10 mM (10 mM sodium acetate) was used to adjust the pH of the sample liquid to 4.5, 5.0 or 5.5. Further, a sodium borate buffer solution of 10 mM (10 mM disodium tetraborate) was used to adjust the pH to 8.5. Further, a buffer solution of sodium chloride of 1 M-sodium hydroxide of 50 mM (1 M NaCl 50 mM NaOH) was used to adjust the pH to 10.0.

Figure 19:
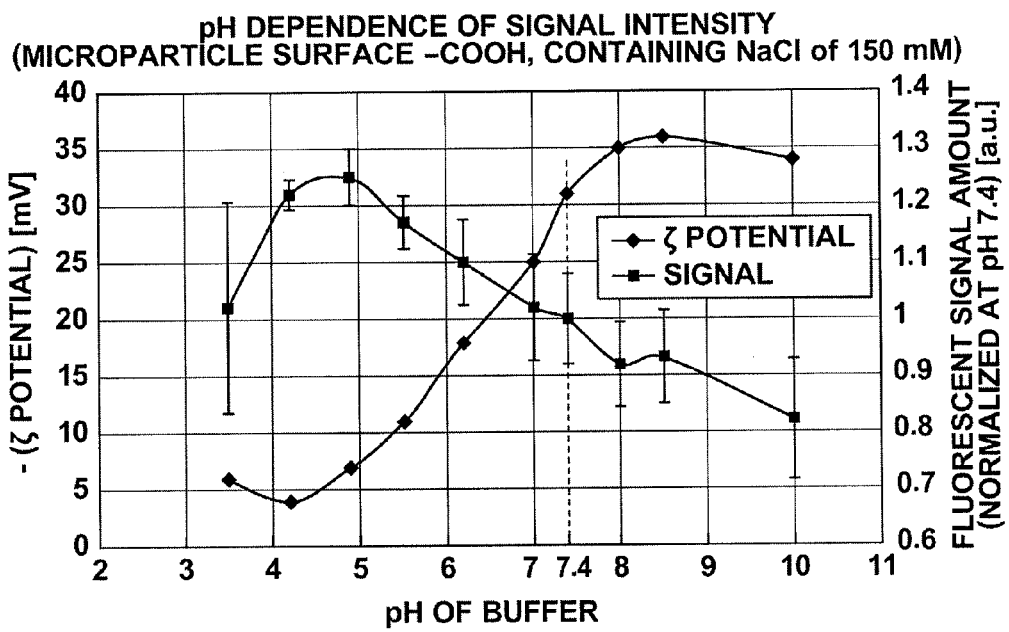
FIG. 19 is a graph showing dependence of fluorescent signal amounts on the pH of buffer.

For each of ten different pH values from pH 3.5 to pH 10, the fluorescent signal amount was measured with respect to six sample cells. FIG. 19 shows dependence of signal intensities on the pH of buffer, which was obtained by the measurement. In FIG. 19, the fluorescent signal amount is normalized at the value of pH 7.4.

As FIG. 19 shows, when the pH of the buffer is 4.5, the fluorescent signal value is at least 1.2 times greater than the value of the fluorescent signal amount obtained when the pH is 7.4. Further, the degree of variation of signals, represented by an error bar, at pH 4.5 is less than or equal to a half of the degree of variation of signals at pH 7.4.

Further, a zeta potential meter (Zetasizer Nano, produced by SYSMEX CORPORATION) was used, and the surface electric potential (zeta ($\zeta$) potential) of the fluorescent substance in each of solutions was measured. The solutions contained the fluorescent substance the surface of which was modified in a manner similar to the aforementioned example, and had pH values at the measurement points in the example as described above. Further, FIG. 19 shows the $\zeta$ potential of the fluorescent substance at each pH value at which fluorescent signal measurement was carried out.

As FIG. 19 shows, it was confirmed that when the surface of a fluorescent substance is modified with COOH, the charge decreases as the pH of the buffer approaches 4, and the charge increases as the pH of the buffer approaches 8.

As FIG. 19 shows, the fluorescent signal amount and the surface electric potential of the fluorescent substance depend on the pH of buffer. Therefore, it is apparent that the fluorescent signal amount increases as the charge on the surface of the fluorescent substance is smaller and that the variation in signals is smaller as the signal values are larger. Accordingly, it was confirmed that the fluorescent signal can be increased and the variation in signals can be suppressed by adjusting the pH.

We consider that as the charge is smaller (electrically more neutral), the hydrophilicity of the fluorescent substance becomes lower, in other words, it becomes hydrophobic. Therefore, as the charge is smaller, the fluorescent substance approaches closer to the sensor surface (the fluorescent substance is attracted to the sensor surface). Therefore, the fluorescent signal increases, and the variation in signals becomes smaller. Further, we consider that the fluorescent signal sharply drops as the pH of the buffer becomes less than 4, because the degree of acidity is too strong and the bond force of the antigen-antibody reaction becomes lower and the bond is even broken.

What is claimed is:

1. A detection method comprising the steps of:
preparing a sensor chip including a dielectric plate and a sensor portion that has at least a metal layer deposited on a surface of the dielectric plate;
binding a fluorescent-label binding substance in an amount corresponding to the amount of a detection target substance contained in a liquid sample to the sensor portion by contacting the liquid sample with the sensor portion;
irradiating the sensor portion with excitation light to generate an enhanced optical field on the sensor portion; and
detecting the amount of the detection target substance based on the amount of light generated by excitation of a fluorescent label contained in the fluorescent-label binding substance, the fluorescent label being excited in the enhanced optical field, wherein a fluorescent substance the charge state of which changes in the liquid sample according to the pH of the liquid sample is used as the fluorescent label, the fluorescent substance containing a plurality of fluorescent dye molecules enclosed by a material that transmits fluorescence output from the plurality of fluorescent dye molecules, and wherein in the state in which the fluorescent-label binding substance has bound to the sensor portion, the fluorescent substance is attracted to a surface of the sensor portion by adjusting the pH of the liquid sample in such a manner to neutralize the charge state of the fluorescent substance, and wherein the amount of the detection target substance is detected in the state in which the fluorescent substance is attracted to the surface of the sensor portion wherein plasmons are excited in the metal layer by irradiation with the excitation light to generate the optical field enhanced by the plasmons, and the amount of detection target substance is detected by detecting, as the light generated by the excitation of the fluorescent label, fluorescence output from the fluorescent label by the excitation of the fluorescent label.

2. A detection method, as defined in claim 1, wherein the particle size of the fluorescent substance is greater than or equal to 30 nm.

3. A detection method, as defined in claim 1, wherein a fluorescent substance the surface of which is modified with a functional group, the charge state of the functional group changing according to the pH of the liquid sample, is used as the fluorescent substance of the fluorescent label, and wherein when the fluorescent-label binding substance binds to the sensor portion, the pH of the liquid sample is adjusted so as to ionize the functional group, and wherein after the fluorescent-label binding substance has bound to the sensor portion, the pH of the liquid sample is adjusted so as to neutralize the functional group, thereby attracting the fluorescent substance to the surface of the sensor portion.

4. A detection method as defined in claim 1, wherein plasmons are excited in the metal layer by irradiation with the excitation light to generate the optical field enhanced by the plasmons, and wherein the amount of the detection target substance is detected by detecting, as the light generated by excitation of the fluorescent label, radiation light that radiates from the other surface of the dielectric plate by newly inducing plasmons in the metal layer by fluorescence output from the fluorescent label by the excitation of the fluorescent label.

5. A detection method, as defined in claim 1, wherein the sensor chip includes an optical waveguide layer deposited on the metal layer, and wherein an optical waveguide mode is excited in the optical waveguide layer by irradiation with the excitation light to generate the optical field enhanced by the optical waveguide mode.

6. A detection method, as defined in claim 1, wherein the sensor chip includes an optical waveguide layer deposited on the metal layer, and wherein an optical waveguide mode is excited in the optical waveguide layer by irradiation with the excitation light to generate the optical field enhanced by the optical waveguide mode, and wherein the amount of the detection target substance is detected by detecting, as the light generated by excitation of the fluorescent label, radiation light that radiates from the other surface of the dielectric plate, the radiation light radiating by newly inducing plasmons in the metal layer by fluorescence output from the fluorescent label by the excitation of the fluorescent label.

* * * * *